(12) United States Patent
Hoveyda et al.

(10) Patent No.: US 9,840,508 B2
(45) Date of Patent: Dec. 12, 2017

(54) N-ACYL-(3-SUBSTITUTED)-(8-METHYL)-5,6-DIHYDRO-[1,2,4]TRIAZOLO[4,3-A]PYRAZINES AS SELECTIVE NK-3 RECEPTOR ANTAGONISTS, PHARMACEUTICAL COMPOSITION, METHODS FOR USE IN NK-3 RECEPTOR-MEDIATED DISORDERS

(71) Applicant: EUROSCREEN SA, Charleroi (BE)

(72) Inventors: Hamid Hoveyda, Brussels (BE); Guillaume Dutheuil, Vedrin (BE); Graeme Fraser, Bousval (BE)

(73) Assignee: OGED SA, Charleroi (BE)

( * ) Notice: Subject to any disclaimer, the term of this patent is extended or adjusted under 35 U.S.C. 154(b) by 0 days.

(21) Appl. No.: 14/777,543

(22) PCT Filed: Mar. 28, 2014

(86) PCT No.: PCT/EP2014/056372
§ 371 (c)(1),
(2) Date: Sep. 16, 2015

(87) PCT Pub. No.: WO2014/154897
PCT Pub. Date: Oct. 2, 2014

(65) Prior Publication Data
US 2016/0289233 A1    Oct. 6, 2016

(30) Foreign Application Priority Data
Mar. 29, 2013  (EP) .................................. 13161866

(51) Int. Cl.
C07D 487/04    (2006.01)

(52) U.S. Cl.
CPC .................. C07D 487/04 (2013.01)

(58) Field of Classification Search
CPC .................................................. C07D 487/04
See application file for complete search history.

(56) References Cited

U.S. PATENT DOCUMENTS

| | | |
|---|---|---|
| 8,871,761 B2 | 10/2014 | Hoveyda et al. |
| 2008/0275052 A1 | 11/2008 | Dhar et al. |
| 2014/0275097 A1 | 9/2014 | Hoveyda et al. |
| 2014/0371218 A1 | 12/2014 | Hoveyda et al. |
| 2015/0232471 A1 | 8/2015 | Hoveyda et al. |
| 2015/0315199 A1 | 11/2015 | Hoveyda et al. |

FOREIGN PATENT DOCUMENTS

| | | |
|---|---|---|
| WO | 00/43008 A1 | 7/2000 |
| WO | 03/082817 | 10/2003 |
| WO | 2004/021984 | 3/2004 |
| WO | 2005/032464 | 4/2005 |
| WO | 2005/080397 | 9/2005 |
| WO | 2006/120478 A2 | 11/2006 |
| WO | 2007/138351 | 12/2007 |
| WO | 2009/095253 | 8/2009 |
| WO | 2009/095254 | 8/2009 |
| WO | 2010/125101 | 11/2010 |
| WO | 2010/125102 A1 | 11/2010 |
| WO | 2011/121137 A1 | 10/2011 |
| WO | 2013/050424 | 4/2013 |

OTHER PUBLICATIONS

International Search Report dated Apr. 28, 2014, in corresponding PCT application.
Burke et al., "Coexpression of Dynorphin and Neurokinin B Immunoreactivity in the Rat Hypothalamus: Morphologic Evidence of Interrelated Function Within the Arcuate Nucleus", J. Comp. Neurol., vol. 498, No. 5, May 2006, 712-726.
Copel et al., "Activation of neurokinin 3 receptor increases Nav 1.9 current in enteric neurons", J. Physiol., vol. 587, Feb. 2009, pp. 1461-1479.
Dawson et al., "Therapeutic Utility of NK3 Receptor Antagonists for the Treatment of Schizophrenia", Current Pharmaceutical Design, vol. 16, No. 3, Feb. 2010, pp. 344-357.
Fioramonti, J. et al., "Intestinal anti-nociceptive behaviour of NK3 receptor antagonism in conscious rats: evidence to support a peripheral mechanism of action", Neurogastroenterol Motil, vol. 15, Mar. 2003, pp. 363-369.
Giardina et al., "Recent advances in neurokinin-3 receptor antagonists", Exp. Opinion Ther. Patents, vol. 10, No. 6, 2000, pp. 939-960.
Goodman et al., "Evidence That Dynorphin Plays a Major Role in Mediating Progesterone Negative Feedback on Gonadotropin-Releasing Hormone Neurons in Sheep", Endocrinology, vol. 145, No. 6, Jun. 2004, pp. 2959-2967.
Houghton et al., "Effect of the NK3 receptor antagonist, talnetant, on rectal sensory function and compliance in healthy humans", Neurogastroenterol Motil, vol. 19, Feb. 2007, pp. 732-743.
Krajewski et al, "Morphologic Evidence That Neurokinin B Modulates Gonadotropin-Releasing Hormone Secretion via Neurokinin 3 Receptors in the Rat Median Eminence", J. Comp. Neurol., vol. 489, No. 3, Apr. 2005, pp. 372-386.
Lomax et al., "Neurochemical classification of enteric neurons in the guinea-pig distal colon", Cell Tissue Res, vol. 302, Aug. 2000, pp. 59-72.

(Continued)

Primary Examiner — San-Ming Hui
(74) Attorney, Agent, or Firm — Young & Thompson

(57) ABSTRACT

Novel compounds of Formula I

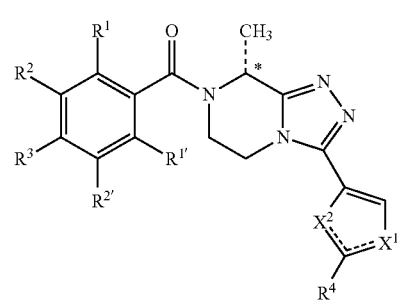

and their use in therapeutic treatments.

12 Claims, No Drawings

(56) References Cited

OTHER PUBLICATIONS

Meltzer et al, "Placebo-Controlled Evaluation of Four Novel Compounds for the Treatment of Schizophrenia and Schizoaffective Disorder", Am. J. Psychiatry, vol. 161, No. 6, Jun. 2004, pp. 975-984.

Murali Dhar et al., "Synthesis and SAR of p38alpha MAP kinase inhibitors based on heterobicyclic scaffolds", Bioorganic Medicinal Chemistry Letters, vol. 17, Jul. 2007, pp. 5019-5024.

Navarro et al., "Regulation of Gonadotropin-Releasing Hormone Secretion by Kisspeptin/Dynorphin/Neurokinin B Neurons in the Arcuate Nucleus of the Mouse", The Journal of Neuroscience, vol. 29, No. 38, Sep. 2009, pp. 11859-11866.

Rick et al., "Combining Growth Hormone-Releasing Hormone Antagonist With Luteinizing Hormone-Releasing Hormone Antagonist Greatly Augments Benign Prostatic Hyperplasia Shrinkage", J. Urol., vol. 187, Apr. 2012, pp. 1498-1504.

Scolnick et al., "Comparative Study of Experimentally Induced Benign and Atypical Hyperplasia in the Ventral Prostate of Different Rat Strains", J. Andrology, vol. 15, No. 4, Jul./Aug. 1994, pp. 287-297.

Shafton et al., "Effects of the peripherally acting NK3 receptor antagonist, SB-235375, on intestinal and somatic nociceptive responses and on intestinal motility in anaesthetized rats", Neurogastroenterol Motil, vol. 16, Oct. 2003, pp. 223-231.

Bottomley et al. "Structural and functional analysis of the human HDAC4 catalytic domain reveals a regulatory structural zinc-binding domain", J. Biol. Chem., vol. 283, No. 39, Sep. 2008, pp. 26694-26704.

Specification and Claims of U.S. Appl. No. 14/781,180, filed Sep. 29, 2015.

International Search Report corresponding to PCT/EP2011/055218, dated Jun. 8, 2011.

International Search Report corresponding to PCT/EP2012/069546, dated Nov. 29, 2012.

International Search Report corresponding to PCT/EP2014/056367, dated Apr. 28, 2014.

International Search Report corresponding to PCT/EP2014/056369, dated Apr. 28, 2014.

N-ACYL-(3-SUBSTITUTED)-(8-METHYL)-5,6-DIHYDRO-[1,2,4]TRIAZOLO[4,3-A] PYRAZINES AS SELECTIVE NK-3 RECEPTOR ANTAGONISTS, PHARMACEUTICAL COMPOSITION, METHODS FOR USE IN NK-3 RECEPTOR-MEDIATED DISORDERS

FIELD OF INVENTION

The present invention relates to novel N-acyl-(3-substituted)-(8-methyl)-5,6-dihydro-[1,2,4]triazolo[4,3-a]pyrazines including their pharmaceutically acceptable solvates that are selective antagonists to neurokinin-3 receptor (NK-3) and are useful as therapeutic compounds, particularly in the treatment and/or prevention of a broad array of CNS and peripheral diseases or disorders.

BACKGROUND OF INVENTION

Tachykinin receptors are the targets of a family of structurally related peptides which include substance P (SP), neurokinin A (NKA) and neurokinin B (NKB), named collectively "tachykinins". Tachykinins are synthesized in the central nervous system (CNS) and peripheral tissues, where they exert a variety of biological activities. Three tachykinin receptors are known which are named neurokinin-1 (NK-1), neurokinin-2 (NK-2) and neurokinin-3 (NK-3) receptors. Tachykinin receptors belong to the rhodopsin-like seven membrane G-protein coupled receptors. SP has the highest affinity and is believed to be the endogenous ligand of NK-1, NKA for NK-2 receptor and NKB for NK-3 receptor, although cross-reactivity amongst these ligands does exist. The NK-1, NK-2 and NK-3 receptors have been identified in different species. NK-1 and NK-2 receptors are expressed in a wide variety of peripheral tissues and NK-1 receptors are also expressed in the CNS; whereas NK-3 receptors are primarily expressed in the CNS.

The neurokinin receptors mediate a variety of tachykinin-stimulated biological effects that include transmission of excitatory neuronal signals in the CNS and periphery (e.g. pain), modulation of smooth muscle contractile activity, modulation of immune and inflammatory responses, induction of hypotensive effects via dilatation of the peripheral vasculature and stimulation of endocrine and exocrine gland secretions.

In the CNS, the NK-3 receptor is expressed in regions including the medial prefrontal cortex, the hippocampus, the thalamus and the amygdala. Moreover, NK-3 receptors are expressed on dopaminergic neurons. Activation of NK-3 receptors has been shown to modulate dopamine, acetylcholine and serotonin release suggesting a therapeutic utility for NK-3 receptor modulators for the treatment of a variety of disorders including psychotic disorders, anxiety, depression, schizophrenia as well as obesity, pain or inflammation (Giardina et al., Exp. Opinion Ther. Patents, 2000, 10(6), 939-960; Current Opinion in Investigational Drugs, 2001, 2(7), 950-956 and Dawson and Smith, Current Pharmaceutical Design, 2010, 16, 344-357).

Schizophrenia is classified into subgroups. The paranoid type is characterized by delusions and hallucinations and absence of thought disorder, disorganized behavior, and affective flattening. In the disorganized type, which is also named 'hebephrenic schizophrenia' in the International Classification of Diseases (ICD), thought disorder and flat affect are present together. In the catatonic type, prominent psychomotor disturbances are evident, and symptoms may include catatonic stupor and waxy flexibility. In the undifferentiated type, psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as a lack of sustained attention and deficits in decision making. The current antipsychotic drugs (APDs) are fairly successful in treating the positive symptoms but fare less well for the negative and cognitive symptoms. Contrary to that, NK-3 antagonists have been shown clinically to improve on both positive and negative symptoms in schizophrenics (Meltzer et al, Am. J. Psychiatry, 2004, 161, 975-984) and ameliorate cognitive behavior of schizophrenics (Curr. Opion. Invest. Drug, 2005, 6, 717-721).

In rat, morphological studies provide evidence for putative interactions between NKB neurons and the hypothalamic reproductive axis (Krajewski et al, J. Comp. Neurol., 2005, 489(3), 372-386). In arcuate nucleus neurons, NKB expression co-localizes with estrogen receptor α and dynorphin, implicated in progesterone feedback to Gonadotropin Releasing Hormone (GnRH) secretion (Burke et al., J. Comp. Neurol., 2006, 498(5), 712-726; Goodman et al., Endocrinology, 2004, 145(6), 2959-2967). Moreover, NK-3 receptor is highly expressed in the hypothalamic arcuate nucleus in neurons which are involved in the regulation of GnRH release.

WO 00/43008 discloses a method of suppressing gonadotropin and/or androgen production with specific NK-3 receptor antagonists. More particularly, the WO 00/43008 application relates to lowering luteinizing hormone (LH) blood level by administering an NK-3 receptor antagonist. Concurrently or alternatively with gonadotropin suppression, WO 00/43008 also relates to suppression of androgen production with NK-3 receptor antagonists. Recently it has been postulated that NKB acts autosynaptically on kisspeptin neurons in the arcuate nucleus to synchronize and shape the pulsatile secretion of kisspeptin and drive the release of GnRH from fibers in the median eminence (Navarro et al., J. of Neuroscience, 2009, 23(38), 11859-11866). All these observations suggest a therapeutic utility for NK-3 receptor modulators for sex hormone-dependent diseases.

NK-3 receptors are also found in the human myenteric and submucosal plexus of the sigmoid colon as well as in the gastric fundus (Dass et. al., Gastroenterol., 2002, 122 (Suppl 1), Abstract M1033) with particular expression noted on myenteric intrinsic primary afferent neurons (IPANs) (Lomax and Furness, Cell Tissue Res, 2000, 302, 59-3). Intense stimulation of IPANs changes patterns of intestinal motility and intestinal sensitivity. Electrophysiology experiments have shown that activation of the NK-3 receptor changes the voltage threshold of action potentials in IPANs and promotes the generation of long-lasting plateau potentials (Copel et al., J Physiol, 2009, 587, 1461-1479) that may sensitize these neurons to mechanical and chemical stimuli leading to effects on gut motility and secretion. Similarly, Irritable Bowel Syndrome (IBS) is characterized by patient hypersensitivity to mechanical and chemical stimuli. Thus, NK-3 antagonists have been tested in preclinical models of IBS where they have been shown to be effective to reduce nociceptive behavior caused by colo-rectal distension (Fioramonti et al., Neurogastroenterol Motil, 2003, 15, 363-369; Shafton et al., Neurogastroenterol Motil, 2004, 16, 223-231) and, on this basis, NK-3 antagonists have been advanced into clinical development for the treatment of IBS (Houghton et al., Neurogastroenterol Motil, 2007, 19, 732-743; Dukes et al., Gastroenterol, 2007, 132, A60).

Non-peptide antagonists have been developed for each of the tachykinin receptors. Some of them have been described as dual modulators able to modulate both NK-2 and NK-3 receptors (WO 06/120478). However, known non-peptide NK-3 receptor antagonists suffer from a number of drawbacks, notably poor safety profile and limited CNS penetrability that may limit the success of these compounds in clinical development.

On this basis, new potent and selective antagonists of NK-3 receptor may be of therapeutic value for the preparation of drugs useful in the treatment and/or prevention of CNS and peripheral diseases or disorders in which NKB and the NK-3 receptors are involved.

Target potency alone, which may be demonstrated by competitive binding data, is not sufficient for drug development. Rather, efficacy in vivo is contingent upon achieving a relevant "free" drug concentration relative to the target potency at the physiological site of action. Drug molecules typically bind reversibly to proteins and lipids in plasma. The "free" fraction refers to the drug concentration that is unbound and therefore available to engage the biological target and elicit pharmacological activity. This free fraction is commonly determined using plasma protein binding (PPB) assays. The free drug fraction is relevant to not only achieving the desired pharmacological activity, but also potentially undesirable activities including rapid hepatic metabolism (leading to high first-pass clearance and thereby poor oral bioavailability) as well as possible off-target activities that can lead to safety concerns (for example, inhibition of hERG ion channel activity, a widely accepted marker of cardiovascular toxicity).

The invention thus encompasses compounds of general Formula I, their pharmaceutically acceptable solvates as well as methods of use of such compounds or compositions comprising such compounds as antagonists to the NK-3 receptor. Compounds of Formula I are N-acyl-(3-substituted)-(8-methyl)-5,6-dihydro-[1,2,4]triazolo[4,3-a]pyrazines. The compounds of the invention are generally disclosed in international patent application WO2011/121137 but none is specifically exemplified therein. On another hand, unsubstituted and thus non-chiral 5,6,7,8-tetrahydro [1,2,4]triazolo[4,3-a]pyrazines have been disclosed in WO2010/125102 as modulators of an unrelated target, namely P2X7.

SUMMARY

In a general aspect, the invention provides compounds of general Formula I:

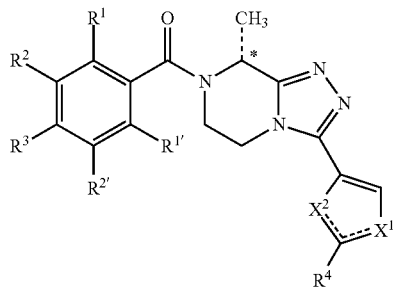

and pharmaceutically acceptable solvates thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl;
$X^1$ is S and $X^2$ is N or $X^1$ is CH and $X^2$ is O;
═══ represents a single or a double bound depending on $X^1$ and $X^2$;
*--- stands for the (R)-enantiomer or for the racemate of compound of Formula I.

In another aspect, the present invention provides a pharmaceutical composition comprising at least one compound according to the invention or a pharmaceutically acceptable solvate thereof.

The invention also relates to the use of the above compounds or their pharmaceutically acceptable solvates as modulators of NK-3 receptors, preferably as antagonists of NK-3 receptors.

The invention also relates to the use of the above compounds or their pharmaceutically acceptable solvates as lowering agents of the circulating LH levels.

The invention further provides methods of treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable solvate of Formula I, to a patient in need thereof. The invention further provides methods of treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable solvate of Formula I, to a patient in need thereof.

Preferably the patient is a warm-blooded animal, more preferably a human.

The invention further provides methods of treatment for gynecological disorders and infertility. In particular, the invention provides methods to lower and/or suppress the LH-surge in assisted conception comprising the administration of a therapeutically effective amount of a compound or pharmaceutically acceptable solvate of Formula I, to a patient in need thereof. Preferably the patient is a warm-blooded animal, more preferably a woman.

The invention further provides methods to affect androgen production to cause male castration and to inhibit the sex drive in male sexual offenders comprising the administration of a therapeutically effective amount of a compound or pharmaceutically acceptable solvate of Formula I, to a patient in need thereof. Preferably the patient is a warm-blooded animal, more preferably a man.

The invention also provides the use of a compound of Formula I or a pharmaceutically acceptable solvate thereof as a medicament. Preferably, the medicament is used for the treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. Preferably, the medicament is used for the treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. The medicament may also be used for the treatment of gynecologic disorders, infertility and to affect androgen production to cause male castration.

DETAILED DESCRIPTION

As noted above, the invention relates to compounds of Formula I:

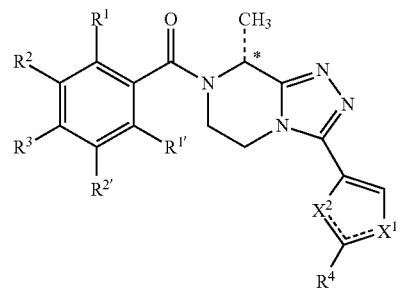

and pharmaceutically acceptable solvates thereof, wherein:

$R^1$ is H or F;

$R^{1'}$ is H;

$R^2$ is H, F or Cl;

$R^{2'}$ is H or F;

$R^3$ is F or Cl;

$R^4$ is methyl or trifluoromethyl;

$X^1$ is S and $X^2$ is N or $X^1$ is CH and $X^2$ is O;

═ represents a single or a double bound depending on $X^1$ and $X^2$;

*--- stands for the (R)-enantiomer or for the racemate of compound of Formula I.

In an embodiment of the invention, compound of Formula I is the (R)-enantiomer. In another embodiment, compound of Formula I is the racemate.

In one embodiment, preferred compounds of Formula I are those of Formula I':

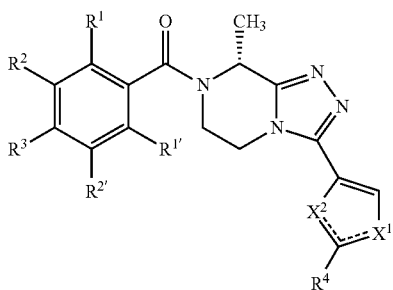

and pharmaceutically acceptable solvates thereof, wherein $R^1$, $R^{1'}$, $R^2$, $R^{2'}$, $R^3$, $R^4$, $X^1$ and $X^2$ are as defined in Formula I and ═══ represents a single or a double bound depending on $X^1$ and $X^2$.

In one embodiment, preferred compounds of Formula I are those of Formula I":

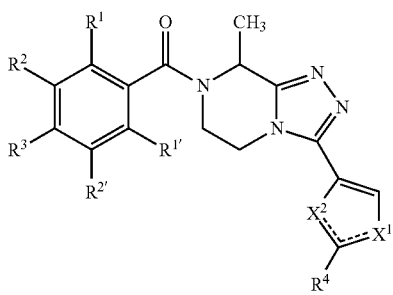

and pharmaceutically acceptable solvates thereof, wherein $R^1$, $R^{1'}$, $R^2$, $R^{2'}$, $R^3$, $R^4$, $X^1$ and $X^2$ are as defined in Formula I and ═══ represents a single or a double bound depending on $X^1$ and $X^2$.

In one embodiment, preferred compounds of Formula I are those of Formula Ia:

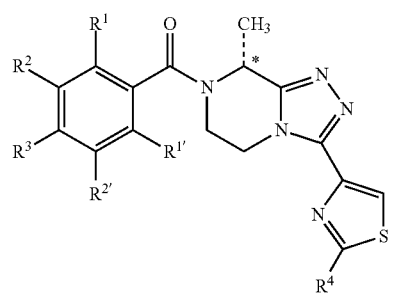

and pharmaceutically acceptable solvates thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl;
*--- stands for the (R)-enantiomer or for the racemate of compound of Formula Ia.

In one embodiment, preferred compounds of Formula Ia are those of Formula Ia':

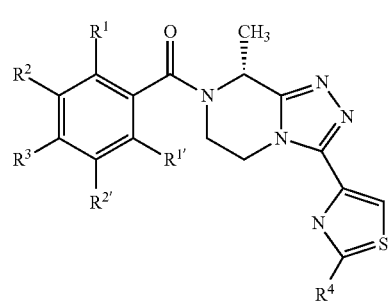

and pharmaceutically acceptable solvates thereof, wherein $R^1$, $R^{1'}$, $R^2$, $R^{2'}$, $R^3$ and $R^4$ are as defined in Formula Ia.

In one embodiment, preferred compounds of Formula I are those of Formula Ib:

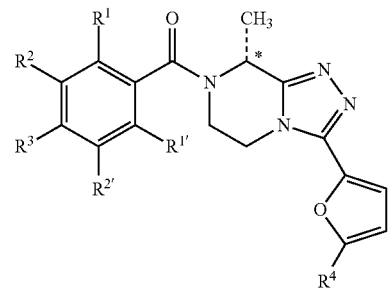

and pharmaceutically acceptable solvates thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl, preferably $R^4$ is methyl;
*--- stands for the (R)-enantiomer or for the racemate of compound of Formula Ib.

In one embodiment, preferred compounds of Formula Ib are those of Formula Ib':

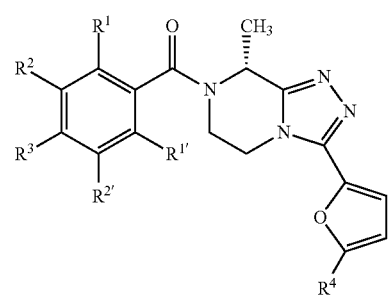

and pharmaceutically acceptable solvates thereof, wherein $R^1$, $R^{1'}$, $R^2$, $R^{2'}$, $R^3$ and $R^4$ are as defined in Formula Ib.

Particularly preferred compounds of Formula I of the invention are those listed in Table 1 hereafter.

TABLE 1

| Cpd n° | Structure | Chemical name | MW |
|---|---|---|---|
| 1 | 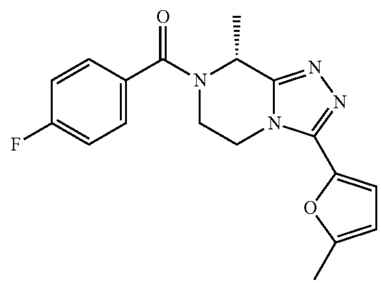 [SMILES: Cc1ccc(-c2nnc3n2CCN(C(=O)c2ccc(F)cc2)[C@@H]3C)o1] | (R)-(4-fluorophenyl)(8-methyl-3-(5-methylfuran-2-yl)-5,6-dihydro-[1,2,4]triazolo[4,3-a]pyrazin-7(8H)-yl)methanone | 340.35 |
| 2 | 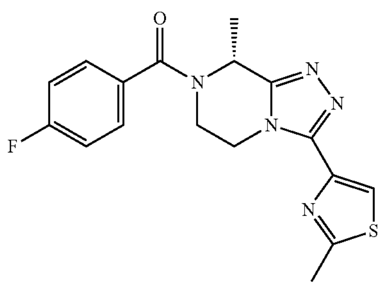 [SMILES: Cc1nc(-c2nnc3n2CCN(C(=O)c2ccc(F)cc2)[C@@H]3C)cs1] | (R)-(4-fluorophenyl)(8-methyl-3-(2-methylthiazol-4-yl)-5,6-dihydro-[1,2,4]triazolo[4,3-a]pyrazin-7(8H)-yl)methanone | 357.41 |
| 3 | 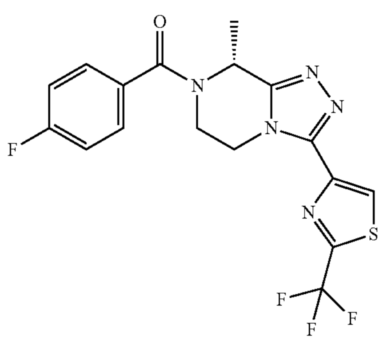 [SMILES: C[C@@H]1c2nnc(-c3csc(C(F)(F)F)n3)n2CCN1C(=O)c1ccc(F)cc1] | (R)-(4-fluorophenyl)(8-methyl-3-(2-(trifluoromethyl)thiazol-4-yl)-5,6-dihydro-[1,2,4]triazolo[4,3-a]pyrazin-7(8H)-yl)methanone | 411.38 |
| 4 | 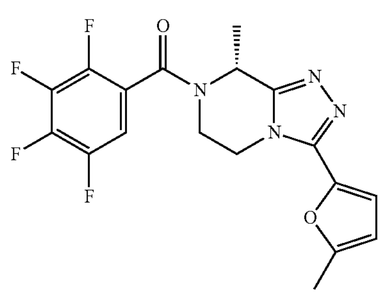 [SMILES: Cc1ccc(-c2nnc3n2CCN(C(=O)c2cc(F)c(F)c(F)c2F)[C@@H]3C)o1] | (R)-(8-methyl-3-(5-methylfuran-2-yl)-5,6-dihydro-[1,2,4]triazolo[4,3-a]pyrazin-7(8H)-yl)(2,3,4,5-tetrafluorophenyl)methanone | 394.32 |
| 5 | 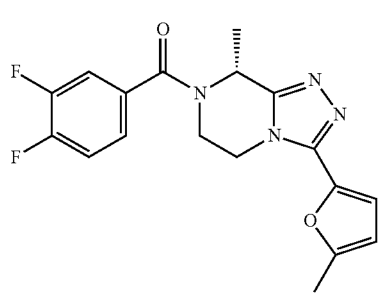 [SMILES: Cc1ccc(-c2nnc3n2CCN(C(=O)c2ccc(F)c(F)c2)[C@@H]3C)o1] | (R)-(3,4-difluorophenyl)(8-methyl-3-(5-methylfuran-2-yl)-5,6-dihydro-[1,2,4]triazolo[4,3-a]pyrazin-7(8H)-yl)methanone | 358.34 |

TABLE 1-continued

| Cpd n° | Structure | Chemical name | MW |
|---|---|---|---|
| 6 | 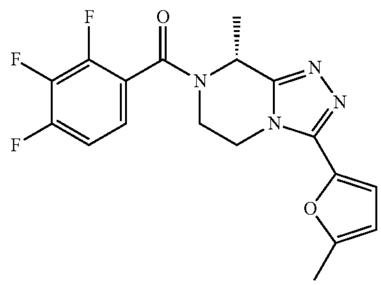 [SMILES: Cc1ccc(-c2nnc3n2CCN(C(=O)c2ccc(F)c(F)c2F)[C@@H]3C)o1] | (R)-(8-methyl-3-(5-methylfuran-2-yl)-5,6-dihydro-[1,2,4]triazolo[4,3-a]pyrazin-7(8H)-yl)(2,3,4-trifluorophenyl)methanone | 376.33 |
| 7 | 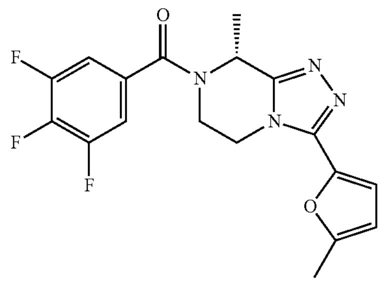 [SMILES: Cc1ccc(-c2nnc3n2CCN(C(=O)c2cc(F)c(F)c(F)c2)[C@@H]3C)o1] | (R)-(8-methyl-3-(5-methylfuran-2-yl)-5,6-dihydro-[1,2,4]triazolo[4,3-a]pyrazin-7(8H)-yl)(3,4,5-trifluorophenyl)methanone | 376.33 |
| 8 | 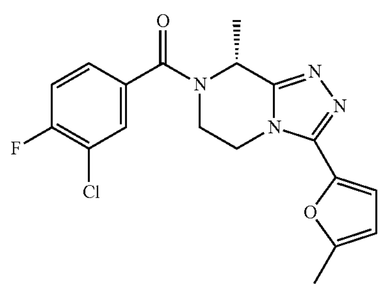 [SMILES: Cc1ccc(-c2nnc3n2CCN(C(=O)c2ccc(F)c(Cl)c2)[C@@H]3C)o1] | (R)-(3-chloro-4-fluorophenyl)(8-methyl-3-(5-methylfuran-2-yl)-5,6-dihydro-[1,2,4]triazolo[4,3-a]pyrazin-7(8H)-yl)methanone | 374.80 |
| 9 | 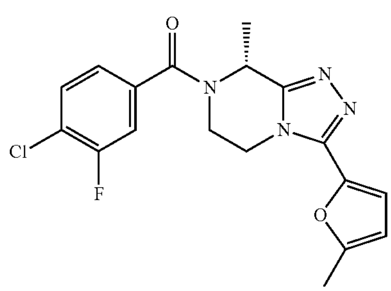 [SMILES: Cc1ccc(-c2nnc3n2CCN(C(=O)c2ccc(Cl)c(F)c2)[C@@H]3C)o1] | (R)-(4-chloro-3-fluorophenyl)(8-methyl-3-(5-methylfuran-2-yl)-5,6-dihydro-[1,2,4]triazolo[4,3-a]pyrazin-7(8H)-yl)methanone | 374.80 |
| 10 | 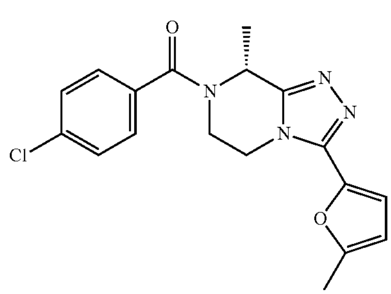 [SMILES: Cc1ccc(-c2nnc3n2CCN(C(=O)c2ccc(Cl)cc2)[C@@H]3C)o1] | (R)-(4-chlorophenyl)(8-methyl-3-(5-methylfuran-2-yl)-5,6-dihydro-[1,2,4]triazolo[4,3-a]pyrazin-7(8H)-yl)methanone | 356.81 |

TABLE 1-continued

| Cpd n° | Structure | Chemical name | MW |
|---|---|---|---|
| 11 | 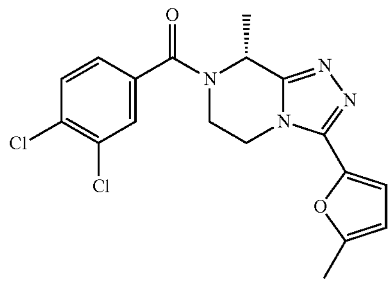 [SMILES: Cc1ccc(-c2nnc3n2CCN(C(=O)c2ccc(Cl)c(Cl)c2)[C@@H]3C)o1] | (R)-(3,4-dichlorophenyl)(8-methyl-3-(5-methylfuran-2-yl)-5,6-dihydro-[1,2,4]triazolo[4,3-a]pyrazin-7(8H)-yl)methanone | 391.25 |
| 12 | 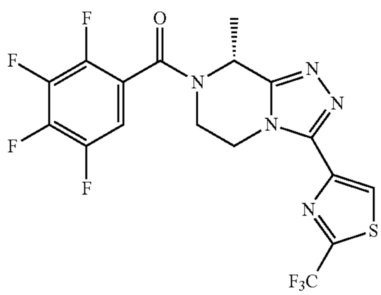 [SMILES: C[C@@H]1c2nnc(-c3csc(C(F)(F)F)n3)n2CCN1C(=O)c1cc(F)c(F)c(F)c1F] | (R)-(8-methyl-3-(2-(trifluoromethyl)thiazol-4-yl)-5,6-dihydro-[1,2,4]triazolo[4,3-a]pyrazin-7(8H)-yl)(2,3,4,5-tetrafluorophenyl)methanone | 465.35 |
| 13 | 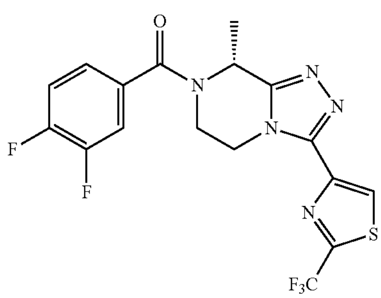 [SMILES: C[C@@H]1c2nnc(-c3csc(C(F)(F)F)n3)n2CCN1C(=O)c1ccc(F)c(F)c1] | (R)-(3,4-difluorophenyl)(8-methyl-3-(2-(trifluoromethyl)thiazol-4-yl)-5,6-dihydro-[1,2,4]triazolo[4,3-a]pyrazin-7(8H)-yl)methanone | 429.37 |
| 14 | 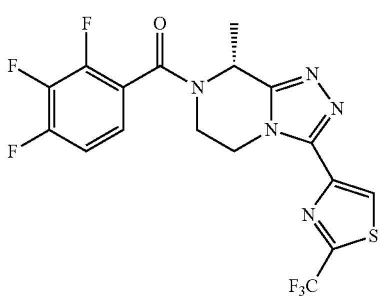 [SMILES: C[C@@H]1c2nnc(-c3csc(C(F)(F)F)n3)n2CCN1C(=O)c1ccc(F)c(F)c1F] | (R)-(8-methyl-3-(2-(trifluoromethyl)thiazol-4-yl)-5,6-dihydro-[1,2,4]triazolo[4,3-a]pyrazin-7(8H)-yl)(2,3,4-trifluorophenyl)methanone | 447.36 |
| 15 | 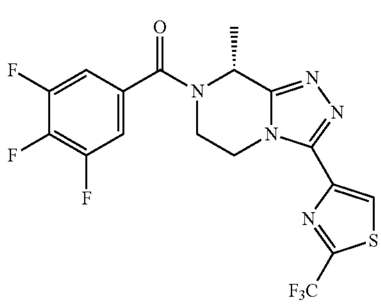 [SMILES: C[C@@H]1c2nnc(-c3csc(C(F)(F)F)n3)n2CCN1C(=O)c1cc(F)c(F)c(F)c1] | (R)-(8-methyl-3-(2-(trifluoromethyl)thiazol-4-yl)-5,6-dihydro-[1,2,4]triazolo[4,3-a]pyrazin-7(8H)-yl)(3,4,5-trifluorophenyl)methanone | 447.36 |

TABLE 1-continued

| Cpd n° | Structure | Chemical name | MW |
|---|---|---|---|
| 16 | 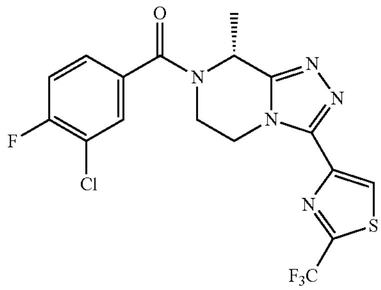 [SMILES: C[C@@H]1c2nnc(-c3csc(C(F)(F)F)n3)n2CCN1C(=O)c1ccc(F)c(Cl)c1] | (R)-(3-chloro-4-fluorophenyl)(8-methyl-3-(2-(trifluoromethyl)thiazol-4-yl)-5,6-dihydro-[1,2,4]triazolo[4,3-a]pyrazin-7(8H)-yl)methanone | 445.82 |
| 17 | 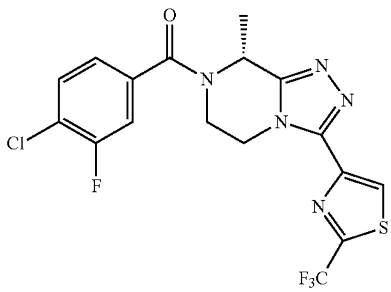 [SMILES: C[C@@H]1c2nnc(-c3csc(C(F)(F)F)n3)n2CCN1C(=O)c1ccc(Cl)c(F)c1] | (R)-(4-chloro-3-fluorophenyl)(8-methyl-3-(2-(trifluoromethyl)thiazol-4-yl)-5,6-dihydro-[1,2,4]triazolo[4,3-a]pyrazin-7(8H)-yl)methanone | 445.82 |
| 18 | | (R)-(4-chlorophenyl)(8-methyl-3-(2-(trifluoromethyl)thiazol-4-yl)-5,6-dihydro-[1,2,4]triazol[4,3-a]pyrazin-7(8H)-yl)methanone | 427.83 | and pharmaceutically acceptable solvate thereof.

In Table 1, the term "Cpd" means compound.

The compounds of Table 1 were named using ChemBioDraw® Ultra version 12.0 (PerkinElmer).

The compounds of Formula I can be prepared by different ways with reactions known to a person skilled in the art.

The invention further relates to a process of manufacturing of compounds of Formula I:

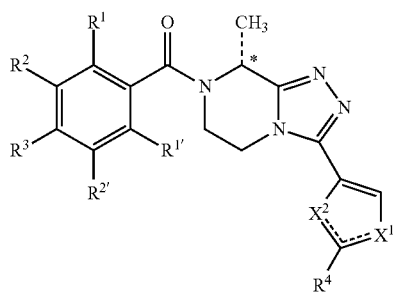

and pharmaceutically acceptable solvates thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl;
$X^1$ is S and $X^2$ is N or $X^1$ is CH and $X^2$ is O;
═══ represents a single or a double bound depending on $X^1$ and $X^2$;
*--- stands for the (R)-enantiomer or for the racemate of compound of Formula I;

characterized in that it comprises the following steps:

a) reacting a compound of Formula (i)

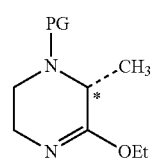

wherein:
PG represents a suitable protecting group such as for example DMB, PMB, Boc, preferably PG is DMB;
*--- stands for the (R)-enantiomer or for the racemate;

with a compound of Formula (ii)

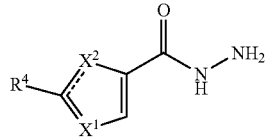

wherein:

R⁴ is as defined above;

X¹ and X² are as defined above;

═ represents a single or a double bound depending on X¹ and X² so as to obtain a compound of Formula (iii)

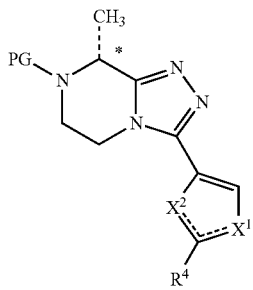

wherein PG, R⁴, X¹ and X² are as defined above, $\overset{*}{-}\, -$ stands for the (R)-enantiomer or for the racemate and ═ represents a single or a double bound depending on X¹ and X²;

b) deprotecting compound of Formula (iii) with a suitable deprotection agent to afford compound of Formula (iv)

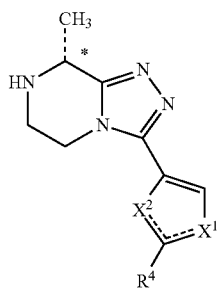

wherein R⁴, X¹ and X² are as defined above, $\overset{*}{-}\, -$ stands for the (R)-enantiomer or for the racemate and ═ represents a single or a double bound depending on X¹ and X²;

c) N-acylating compound of Formula (iv) with a compound of Formula (v)

(v)

wherein R¹, R¹', R², R²' and R³ are as defined above; to afford compound of Formula I as described above.

In a preferred embodiment, the protecting group PG used in the process of the invention is DMB.

Reaction schemes as described in the example section are illustrative only and should not be construed as limiting the invention in any way. According to one embodiment, compounds of Formula I can be prepared using the chiral synthesis of the invention detailed in the examples below.

The invention is further directed to the use of the compounds of the invention or pharmaceutically acceptable solvates thereof as antagonists to the NK-3 receptor.

Accordingly, in a particularly preferred embodiment, the invention relates to the use of compounds of Formula I and subformulae in particular those of Table 1 above, or pharmaceutically acceptable solvates thereof, as NK-3 receptor antagonists.

Accordingly, in another aspect, the invention relates to the use of these compounds or solvates thereof for the synthesis of pharmaceutical active ingredients, such as selective NK-3 receptor antagonists.

USES

The compounds of the invention are therefore useful as medicaments, in particular in the prevention and/or treatment of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. The compounds of the invention are therefore useful as medicaments, in particular in the prevention and/or treatment of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

The invention also provides for a method for delaying in patient the onset of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia, prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a pharmaceutically effective amount of a compound of Formula I or pharmaceutically acceptable solvate thereof to a patient in need thereof. The invention also provides for a method for delaying in patient the onset of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a pharmaceutically effective amount of a compound of Formula I or pharmaceutically acceptable solvate thereof to a patient in need thereof.

Preferably, the patient is a warm-blooded animal, more preferably a human.

The compounds of the invention are especially useful in the treatment and/or prevention of sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable solvate of Formula I, to a patient in need thereof. The compounds of the invention are especially useful in the treatment and/or prevention of sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

In a specific embodiment, the compounds of the invention are especially useful in the treatment and/or prevention of benign prostatic hyperplasia (BPH), endometriosis, uterine fibrosis, uterine fibroid tumor, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. In a specific embodiment, the compounds of the invention are especially useful in the treatment and/or prevention of benign prostatic hyperplasia (BPH), endometriosis, uterine fibrosis, uterine fibroid tumor, uterine leiomyoma, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

In a specific embodiment, the compounds of the invention are especially useful in the treatment and/or prevention of endometriosis, uterine fibrosis, uterine fibroid tumor, uterine leiomyoma, polycystic ovary syndrome (PCOS) and benign prostatic hyperplasia (BPH).

In a specific embodiment, the compounds of the invention are especially useful in the treatment and/or prevention of endometriosis.

In a specific embodiment, the compounds of the invention are especially useful in the treatment and/or prevention of uterine fibrosis.

In a specific embodiment, the compounds of the invention are especially useful in the treatment and/or prevention of uterine fibroid tumor.

In a specific embodiment, the compounds of the invention are especially useful in the treatment and/or prevention of uterine leiomyoma.

In a specific embodiment, the compounds of the invention are especially useful in the treatment and/or prevention of polycystic ovary syndrome (PCOS).

In a specific embodiment, the compounds of the invention are especially useful in the treatment and/or prevention of benign prostatic hyperplasia (BPH).

In a specific embodiment, the compounds of the invention are especially useful in the treatment and/or prevention of hot flashes also known as hot flushes.

In a specific embodiment, the compounds of the invention are especially useful in the treatment and/or prevention of peri-menopausal conditions (i.e. 'hot flashes'), in vitro fertilization ('IVF'), male contraceptive, female contraceptive, castration of sex offenders.

The compounds of the invention are also useful in the treatment of gynecological disorders and infertility. In particular, the invention provides methods to lower and/or suppress the LH-surge in assisted conception.

The compounds of the invention are also useful to cause male castration and to inhibit the sex drive in men. This is of particular interest in the treatment of male sexual offenders.

The invention further provides the use of a compound of Formula I or a pharmaceutically acceptable solvate thereof for the manufacture of a medicament for treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis in a patient. The invention further provides the use of a compound of Formula I or a pharmaceutically acceptable solvate thereof for the manufacture of a medicament for treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis in a patient.

Preferably, the patient is a warm-blooded animal, more preferably a human.

The invention especially provides the use of a compound of Formula I or a pharmaceutically acceptable solvate thereof for the manufacture of a medicament to treat and/or prevent sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable solvate of Formula I, to a patient in need thereof. The invention especially provides the use of a compound of Formula I or a pharmaceutically acceptable solvate thereof for the manufacture of a medicament to treat and/or prevent sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

In a specific embodiment, compounds of Formula I or a pharmaceutically acceptable solvate thereof may be used for the manufacture of a medicament to treat and/or prevent endometriosis, uterine fibrosis, uterine fibroid tumor, uterine leiomyoma, polycystic ovary syndrome (PCOS) and benign prostatic hyperplasia (BPH).

In a specific embodiment, compounds of Formula I or a pharmaceutically acceptable solvate thereof may be used for the manufacture of a medicament to treat and/or prevent endometriosis.

In a specific embodiment, compounds of Formula I or a pharmaceutically acceptable solvate thereof may be used for the manufacture of a medicament to treat and/or prevent uterine fibrosis.

In a specific embodiment, compounds of Formula I or a pharmaceutically acceptable solvate thereof may be used for the manufacture of a medicament to treat and/or prevent uterine fibroid tumor.

In a specific embodiment, compounds of Formula I or a pharmaceutically acceptable solvate thereof may be used for the manufacture of a medicament to treat and/or prevent uterine leiomyoma.

In a specific embodiment, compounds of Formula I or a pharmaceutically acceptable solvate thereof may be used for the manufacture of a medicament to treat and/or prevent polycystic ovary syndrome (PCOS).

In a specific embodiment, compounds of Formula I or a pharmaceutically acceptable solvate thereof may be used for the manufacture of a medicament to treat and/or prevent benign prostatic hyperplasia (BPH).

In a specific embodiment, compounds of Formula I or a pharmaceutically acceptable solvate thereof may be used for the manufacture of a medicament to treat and/or prevent hot flashes also knows as hot flushes.

The invention further provides the use of a compound of Formula I or a pharmaceutically acceptable solvate thereof for the manufacture of a medicament to lower and/or suppress the LH-surge in assisted conception in a patient. Preferably the patient is a warm-blooded animal, more preferably a woman.

The invention further provides the use of a compound of Formula I or a pharmaceutically acceptable solvate thereof for the manufacture of a medicament to cause male castration and to inhibit the sex drive in men. This is of particular interest in the treatment of male sexual offenders.

The invention further provides the use of a compound of Formula I or a pharmaceutically acceptable solvate thereof for the manufacture of a medicament to treat and/or prevent sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable solvate of Formula I, to a patient in need thereof.

According to a further feature of the present invention there is provided a method for modulating NK-3 receptor activity, in a patient, preferably a warm blooded animal, and even more preferably a human, in need of such treatment, which comprises administering to said patient an effective amount of compound of the present invention, or a pharmaceutically acceptable solvate thereof.

According to one embodiment, the compounds of the invention, their pharmaceutical acceptable solvates may be administered as part of a combination therapy. Thus, are included within the scope of the present invention embodiments comprising coadministration of, and compositions and medicaments which contain, in addition to a compound of the present invention, a pharmaceutically acceptable solvate thereof as active ingredient, additional therapeutic agents and/or active ingredients. Such multiple drug regimens, often referred to as "combination therapy", may be used in the treatment and/or prevention of any of the diseases or conditions mediated by or associated with NK-3 receptor modulation. The use of such combinations of therapeutic agents is especially pertinent with respect to the treatment of the above-mentioned disorders within a patient in need of treatment or one at risk of becoming such a patient.

In addition to the requirement of therapeutic efficacy, which may necessitate the use of active agents in addition to the NK-3 receptor modulator compounds of Formula I or pharmaceutical acceptable solvates thereof, there may be additional rationales which compel or highly recommend the use of combinations of drugs involving active ingredients which represent adjunct therapy, i.e., which complement and supplement the function performed by the NK-3 receptor modulator compounds of the present invention. Suitable supplementary therapeutic agents used for the purpose of auxiliary treatment include drugs which, instead of directly treating or preventing a disease or condition mediated by or associated with NK-3 receptor modulation, treat diseases or conditions which directly result from or indirectly accompany the basic or underlying NK-3 receptor modulated disease or condition.

According to a further feature of the present invention, the compound of Formula I, a pharmaceutically acceptable solvate thereof may be used in combination therapy with antipsychotic drugs (APD), to improve the efficacy and to minimize secondary effects associated to APD including but not limited to Dopamine 2/3 and 5-HT2 receptors antagonists. More particular the compound of Formula I, a pharmaceutically acceptable solvate thereof may be used as an adjunct therapy in combination with an atypical antipsychotic drug, including but not limited to risperidone, clozapine, olanzapine, where the NK-3 receptor modulator may serve a role as dose-limiting for the atypical antipsychotic and therefore spare the patient from some of the side effect of those atypical antipsychotic drugs.

Thus, the methods of treatment and pharmaceutical compositions of the present invention may employ the compounds of Formula I or pharmaceutical acceptable solvates thereof in the form of monotherapy, but said methods and compositions may also be used in the form of multiple therapy in which one or more compounds of Formula I or their pharmaceutically acceptable solvates are coadministered in combination with one or more other therapeutic agents.

In the above-described embodiment combinations of the present invention, the compound of Formula I, a pharmaceutically acceptable solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising a compound of Formula I or a pharmaceutically acceptable solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable solvate thereof as active ingredient, additional therapeutic agents and/or active ingredients.

Another object of this invention is a medicament comprising at least one compound of the invention, or a pharmaceutically acceptable solvate thereof, as active ingredient.

According to a further feature of the present invention there is provided the use of a compound of Formula I or a pharmaceutically acceptable solvate thereof for the manufacture of a medicament for modulating NK-3 receptor activity in a patient, in need of such treatment, which comprises administering to said patient an effective amount of compound of the present invention, or a pharmaceutically acceptable solvate thereof.

Preferably, the patient is a warm-blooded animal, more preferably a human.

As set forth above, the compounds of the invention, their pharmaceutically acceptable solvates may be used in monotherapy or in combination therapy. Thus, according to one embodiment, the invention provides the use of a compound of the invention for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, preferably between 2 and 150 mg of at least one compound of the invention, e.g. about 2, 4, 8, 16, 32, 64 or 128 mg per unit dosage. According to another embodiment, such unit dosages will contain between 0.05 and 1000 mg, and usually between 1 and 500 mg, preferably between 2 and 400 mg, preferably between 2 and 200 mg of at least one compound of the invention per unit dosage.

Usually, depending on the condition to be prevented or treated and the route of administration, the active compound of the invention will usually be administered between 0.001 and 10 mg per kilogram body weight, more often between 0.01 and 4 mg per kilogram body weight, preferably between 0.02 and 1.5 mg per kilogram body weight, for example about 0.02, 0.04, 0.08, 0.16, 0.32, 0.64, or 1.28 mg, per kilogram body weight of the patient per day, which may be administered as a single daily dose, divided over one or more daily doses, or essentially continuously, e.g. using a drip infusion. According to another embodiment, the active compound of the invention will usually be administered between 0.001 and 10 mg per kilogram body weight, more often between 0.01 and 7 mg per kilogram body weight, preferably between 0.03 and 3.5 mg per kilogram body weight of the patient per day, which may be administered as a single daily dose, divided over one or more daily doses, or essentially continuously, e.g. using a drip infusion.

According to one embodiment, the active compound of the invention will be administered as a single daily dose, divided over one, two or more daily doses, or essentially continuously, e.g. using a drip infusion.

DEFINITIONS

The definitions and explanations below are for the terms as used throughout the entire application, including both the specification and the claims.

When describing the compounds of the invention, the terms used are to be construed in accordance with the following definitions, unless indicated otherwise.

The ring atoms of (3-substituted)-(8-methyl)-5,6-dihydro-[1,2,4]triazolo[4,3-a]pyrazines of the invention are numbered based on scheme below.

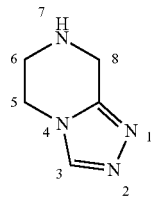

Bonds from an asymmetric carbon in compounds are generally depicted using a solid line ( —— ), a solid wedge ( ▬■ ), or a dotted wedge ( ⋯⋯ ). The use of either a solid or dotted wedge to depict bonds from an asymmetric carbon atom is meant to indicate that only the stereoisomer shown is meant to be included.

The compounds of Formula I and subformulae thereof contain a stereogenic carbon center at position 8 and thus may exist as (R)- and (S)-enantiomers. In an embodiment of the invention, compounds of Formula I are not pure (S)-enantiomers relative to the C8 position.

In the compounds of the invention, a dotted wedge ( ⋯⋯ ) carrying a substituent at the C8 position is used to depict the (R)-enantiomer, thus excluding racemic mixtures thereof.

In the compounds of the invention, a dotted line with a star next to the C8 position ( *--- ) is used to depict either a dotted wedge ( ⋯⋯ ) to represent the (R)-enantiomer or a solid line ( —— ) to depict the racemic mixture of (R)- and (S)-enantiomer, which is called "racemate".

For instance, (R)-(4-fluorophenyl)(8-methyl-3-(5-methylfuran-2-yl)-5,6-dihydro-[1,2,4]triazolo[4,3-a]pyrazin-7 (8H)-yl)methanone (compound no. 1) is depicted as:

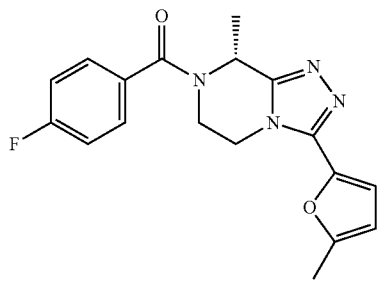

The racemic mixture of this compound, (R)-(4-fluorophenyl)(8-methyl-3-(5-methylfuran-2-yl)-5,6-dihydro-[1,2,4] triazolo[4,3-a]pyrazin-7(8H)-yl)methanone is depicted as:

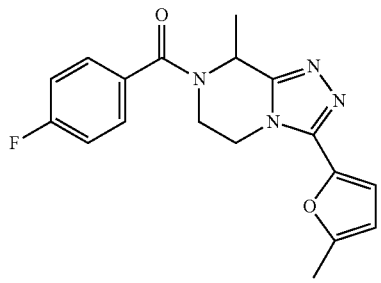

The term "solvate" is used herein to describe a compound in this invention that contains stoichiometric or sub-stoichiometric amounts of one or more pharmaceutically acceptable solvent molecule such as ethanol. The term "hydrate" refers to when the said solvent is water.

All references to compounds of Formula I include references to solvates, multi-component complexes and liquid crystals thereof.

The compounds of the invention include compounds of Formula I as hereinbefore defined, including all polymorphs and crystal habits thereof, prodrugs and prodrugs thereof and isotopically-labeled compounds of Formula I.

The invention also generally covers all pharmaceutically acceptable predrugs and prodrugs of the compounds of Formula I.

The term "prodrug" as used herein means the pharmacologically acceptable derivatives of compounds of Formula I, such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment, as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. NK-3 antagonist) that is sufficient to achieve the desired therapeutic or prophylactic effect in the patient to which/whom it is administered.

The term "administration", or a variant thereof (e.g. "administering"), means providing the active agent or active ingredient (e.g. a NK-3 antagonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "antagonist" as used herein means a compound that competitively or non-competitively binds to a receptor at the same site as an agonist (for example, the endogenous ligand) and has reversible and competitive binding affinity to a receptor without direct modulation of receptor signaling, but that nonetheless occupies the binding site of an agonist (for example, the endogenous ligand) to thereby block agonist-mediated receptor signaling.

The term "sex hormone-dependent disease" as used herein means a disease which is exacerbated by, or caused by, excessive, inappropriate or unregulated sex hormone production and/or an extraordinary physiological response to sex hormones. Examples of such diseases in men include but are not limited to benign prostatic hyperplasia (BPH), prostatic hyperplasia, metastatic prostatic carcinoma, testicular cancer, androgen dependent acne, male pattern baldness and precocious puberty in boys. Examples of such diseases in women include but are not limited to endometriosis, abnormal puberty, uterine fibrosis, uterine fibroid tumor, uterine leiomyoma, hormone-dependent cancers (ovarian cancer, breast cancer), androgen-producing tumor (virilizing ovarian or adrenal tumor), hyperandrogenism, hirsutism, virilization, polycystic ovary syndrome (PCOS), premenstrual dysphoric disease (PMDD), HAIR-AN syndrome (hyperandrogenism, insulin resistance and acanthosisnigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), menorrhagia and adenomyosis (abnormal endometrial growth within the muscle of the uterus).

The term "Psychotic disorders" as used herein means a group of illnesses that affect the mind. These illnesses alter a patient's ability to think clearly, make good judgments, respond emotionally, communicate effectively, understand reality, and behave appropriately. When symptoms are severe, patient with psychotic disorders have difficulty staying in touch with reality and are often unable to meet the ordinary demands of daily life. Psychotic disorders include but are not limited to, schizophrenia, schizophreniform disorder, schizo-affective disorder, delusional disorder, brief psychotic disorder, shared psychotic disorder, psychotic disorder due to a general medical condition, substance-induced psychotic disorder or psychotic disorders not otherwise specified (Diagnostic and Statistical Manual of Mental Disorders, Ed. 4th, American Psychiatric Association, Washington, D.C. 1994).

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The present invention will be better understood with reference to the following examples. These examples are intended to representative of specific embodiments of the invention, and are not intended as limiting the scope of the invention.

EXAMPLES

Chemistry Examples

All reported temperatures are expressed in degrees Celsius (° C.); all reactions were carried out at room temperature (RT) unless otherwise stated.

All reactions were followed by thin layer chromatography (TLC) analysis (TLC plates, silica gel 60 $F_{254}$, Merck) was used to monitor reactions, establish silica-gel flash chromatography conditions. All other TLC developing agents/visualization techniques, experimental set-up or purification procedures that were used in this invention, when not described in specific details, are assumed to be known to those conversant in the art and are described in such standard reference manuals as: i) Gordon, A. J.; Ford, R. A. "The Chemist's Companion—A Handbook of Practical Data, Techniques, and References", Wiley: New York, 1972; ii) Vogel's Textbook of Practical Organic Chemistry, Pearson Prentice Hall: London, 1989.

HPLC-MS spectra were typically obtained on an Agilent LCMS using electrospray ionization (ESI). The Agilent instrument includes an autosampler 1100, a binary pump 1100, an ultraviolet multi-wavelength detector 1100 and a 6100 single-quad mass-spectrometer. The chromatography column used was Sunfire 3.5 µm, C18, 3.0×50 mm in dimensions.

Eluent typically used was a mixture of solution A (0.1% TFA in $H_2O$) and solution B (0.1% TFA in MeCN).

Gradient was applied at a flow rate of 1.3 mL per minute as follows: gradient A (for analysis of final compounds and intermediates): held the initial conditions of 5% solution B for 0.2 min, increased linearly to 95% solution B in 6 min, held at 95% during 1.75 min, returned to initial conditions in 0.25 min and maintained for 2.0 min; gradient B (for analysis of crude samples and reactions mixtures): held the initial conditions of 5% solution B for 0.2 min, increased linearly to 95% in 2.0 min, held at 95% during 1.75 min, returned to initial conditions in 0.25 min and maintained for 2 min.

Determination of chiral purity was made using chiral HPLC that was performed on an Agilent 1100 (binary pump and a ultraviolet multi wavelength detector) with manual or automatic (Autosampler 1100) injection capabilities. Column used is CHIRALPAK IA 5 µm, 4.6×250 mm 4.6×250 mm in isocratic mode. Choice of eluent was predicated on the specifics of each separation. Further details concerning the chiral HPLC methods used are provided below.

Method A: column CHIRALPAK IA 5 µm, 4.6×250 mm, eluent: EtOAc plus 0.1% of DEA, flow rate: 1.0 mL per minute; UV detection at 254 or 280 nm; column at RT, eluent was used as sample solvent.

Method B: column CHIRALPAK IA 5 µm 4.6×250 mm, eluent: hexane/ethanol (80:20 v/v) plus 0.1% of DEA, flow rate: 1.0 mL per minute; UV detection at 254 or 280 nm, column at RT, eluent was used as sample solvent.

Preparative HPLC purifications were typically carried out on an Agilent 1200 instrument (preparative pump 1200 and ultraviolet multi wavelength detector 1200) with manual injection. The chromatography column used was Waters Sunfire 5 µm, C18, 19×100 mm, or XBridge 5 µm, C18, 19×100 mm depending on the type of eluent system employed, i.e. low pH or high pH conditions.

For high-pH HPLC purifications, eluent typically consisted of a mixture of solution A (0.04 M ammonium bicarbonate in H$_2$O plus 0.1% of conc. NH$_4$OH) and solution B was MeCN. The gradient was adapted depending on the impurity profile in each sample purified, thereby allowing sufficient separation between the impurities and the desired compound.

In rare cases when high-pH HPLC purification did not provide sufficient purity, low-pH HPLC was applied. For low-pH HPLC purifications, eluent typically consisted of a mixture of solution A (0.1% of TFA in H$_2$O) and solution B was MeCN. The gradient was adapted depending on the impurity profile in each sample purified, thereby allowing sufficient separation between the impurities and the desired compound. TFA was removed from evaporated fractions by liquid-liquid extraction.

$^1$H (300 MHz), $^{13}$C NMR (75 MHz) and $^{19}$F NMR (282 MHz) spectra were recorded on a BrukerAvance DRX 300 instrument. Chemical shifts are expressed in parts per million, (ppm, δ units). Coupling constants are expressed in Hertz (Hz). Abbreviations for multiplicities observed in NMR spectra are as follows: s (singlet), d (doublet), t (triplet), q (quadruplet), m (multiplet), br (broad).

Solvents, reagents and starting materials were purchased and used as received from commercial vendors unless otherwise specified.

The following abbreviations are used:
Boc: tert-butoxycarbonyl,
Cpd: compound,
DCM: Dichloromethane,
DEA: diethylamine,
DMB: 2,4-dimethoxybenzyl,
DMB-CHO: 2,4-dimethoxybenzaldehyde,
ee: Enantiomeric excess,
eq.: Equivalent(s),
EtOAc: Ethylacetate,
EtOH: Ethanol,
g: Gram(s),
h: Hour(s),
L: Liter(s),
MeOH: Methanol,
µL: Microliter(s),
mg: Milligram(s),
mL: Milliliter(s),
mmol: Millimole(s),
min: Minute(s),
P: UV purity at 254 nm or 215 nm determined by HPLC-MS,
PMB: 4-methoxybenzyl,
RT: Room temperature,
tBu: tert-Butyl,
TBME: tert-Butyl Methyl Ether,
TFA: trifluoroacetic acid,
TLC: Thin layer chromatography.

The intermediates and compounds described below were named using ChemBioDraw® Ultra version 12.0 (PerkinElmer).

I. Racemic Synthesis

I.1. General Synthetic Scheme for Racemic Synthesis

Compounds of the invention may be synthesized using the methodology described in Scheme 1, which represents the racemic product synthesis. The racemic products may then be subjected to chiral HPLC for chiral separation.

Scheme 1: General racemic synthetic scheme for the preparation of the compounds of the invention.

Step 1

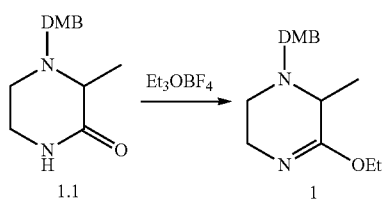

Step 2

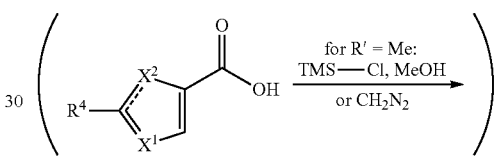

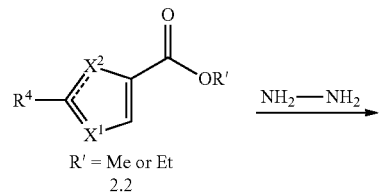

Step 3

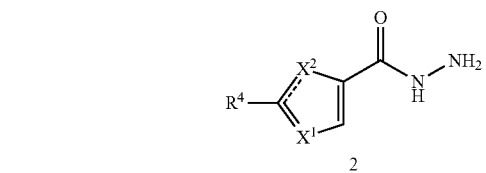

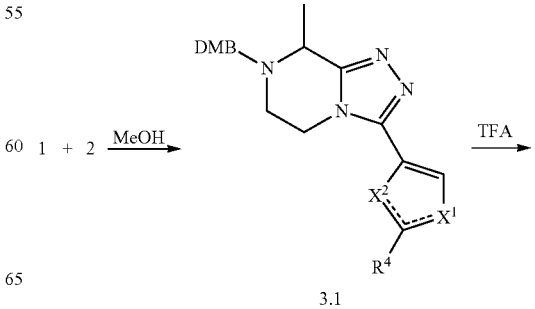

-continued

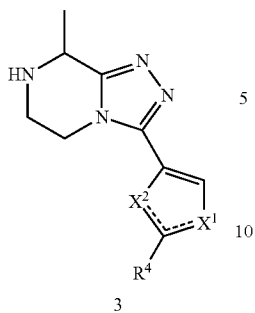
3

Step 4

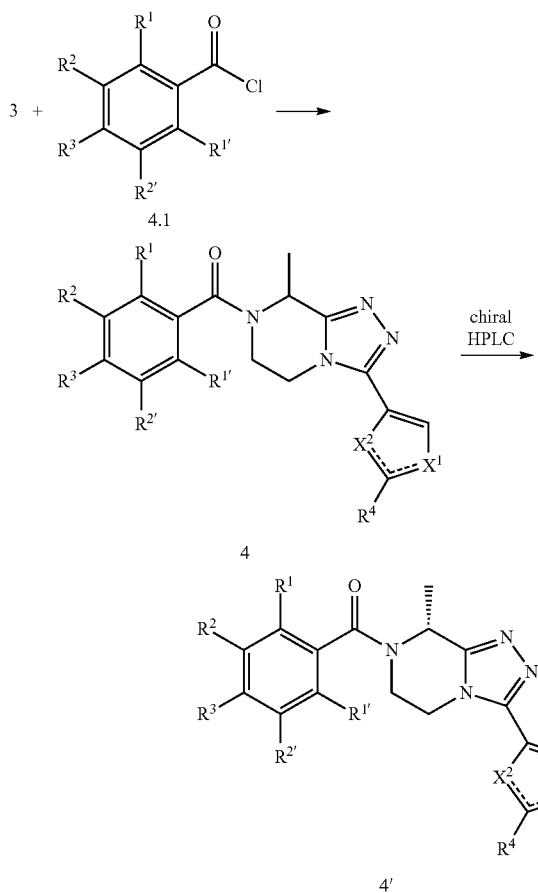

The general synthetic scheme comprises the following steps:

Step 1: DMB-protected ketopiperazine 1.1 was converted to iminoether 1 by using the Meerwein reagent ($Et_3OBF_4$).

Step 2: Ester 2.2 was subsequently converted to acyl hydrazide 2. Ester 2.2 may be obtained be esterification of acid 2.1.

Step 3: Cyclodehydration between the acyl hydrazide 2 and the iminoether 1 furnished the protected triazolopiperazine 3.1. Thereafter, 3.1 was subjected to acidolytic deprotection to obtain 3.

Step 4: The thus obtained triazolopiperazine intermediate 3 was acylated through reaction with the appropriate acid chloride 4.1 to obtain the racemic target structure represented by the general Formula 4. The chiral compound 4' was subsequently obtained by purification using preparative chiral HPLC.

I.2. Step 1: Protection and Conversion to Iminoether 1
Method A: Conversion of DMB-Protected Ketopiperazine 1.1 to Iminoether 1

Method A is the procedure used for the synthesis of the iminoether intermediate 1 with a DMB protecting group and is detailed below:

Scheme 2: Conversion to iminoether 1.

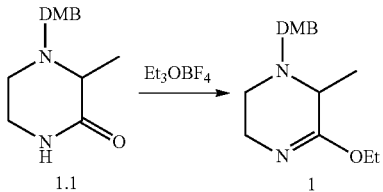

Synthesis of 1-(2,4-dimethoxybenzyl)-5-ethoxy-6-methyl-1,2,3,6-tetrahydropyrazine 1

Oven-dried (115° C.) sodium carbonate (18.6 g, 98 mmol, 2.25 eq.) was placed in a 500 mL round-bottom flask. The round-bottom flask was backfilled with Ar and then capped with a rubber septum. A solution of 4-(2,4-dimethoxybenzyl)-3-methylpiperazin-2-one 1.1 (20.6 g, 78 mmol, 1 eq.) in anhydrous DCM (250 mL) was added, followed by triethyloxoniumtetrafluoroborate (18.6 g, 98 mmol, 1.25 eq.) in one portion. Thereafter, the reaction mixture was stirred further at RT for 1 h whereupon the reaction mixture was diluted with water (250 mL). The aqueous layer was extracted with DCM (3×150 mL). The organic layers were combined, dried over $MgSO_4$, filtered and concentrated under reduced pressure. The crude compound was then purified on silica gel (EtOAc) to afford the desired product 1 as orange oil. Yield: 13.2 g, 58%. LCMS: P=93%, retention time=1.8 min, $(M+H+H_2O)^+$: 311; $^1H$-NMR ($CDCl_3$): δ 7.23 (d, J=8.8 Hz, 1H), 6.48 (d, J=8.8 Hz, 1H), 6.44 (s, 1H), 4.02 (m, 2H), 3.92 (s, 3H), 3.91 (s, 3H), 3.86 (d, $J_{AB}$=14.0 Hz, 1H), 3.46 (d, $J_{AB}$=14.0 Hz, 1H), 3.44 (m, 2H), 3.10 (m, 1H), 2.79 (m, 1H), 2.32 (m, 1H), 1.35 (d, J=6.8 Hz, 3H), 1.24 (t, J=6.0 Hz, 3H).

I.3. Step 2: Formation of Acyl Hydrazide 2
Method B: Acyl Hydrazide 2

Method B is the procedure used for the synthesis of the acyl hydrazides 2 and is detailed below:

Scheme 3: Formation of acylhydrazide 2.

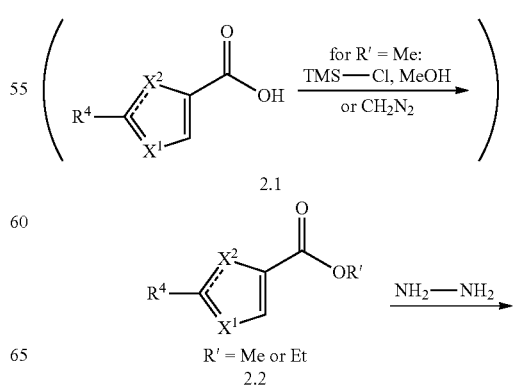

-continued

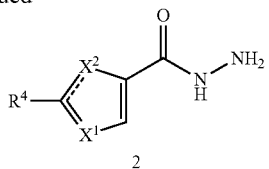

2

In a round-bottom flask equipped with a condenser, ester 2.2 (1 eq.) is dissolved in anhydrous EtOH and treated with hydrazine hydrate (1.2 to 20 eq., preferably 1.5 to 10 eq.) using a temperature range from RT to reflux. After allowing the reaction mixture to come to RT, the solution is concentrated under reduced pressure. Co-evaporations using a mixture of commercial anhydrous DCM:MeOH (1:1) may be performed to remove residual water. The residue is then recrystallized and/or precipitated or purified on a pad of silica to afford 2.

I.4. Step 3: Cyclodehydration Leading to triazolopiperazine 3

Method C: Cyclodehydration and acydolysis

Method C is the procedure used for the synthesis of the triazolopiperazine 3 and is detailed below:

Scheme 4: Cyclodehydration leading to triazolopiperazine 3.

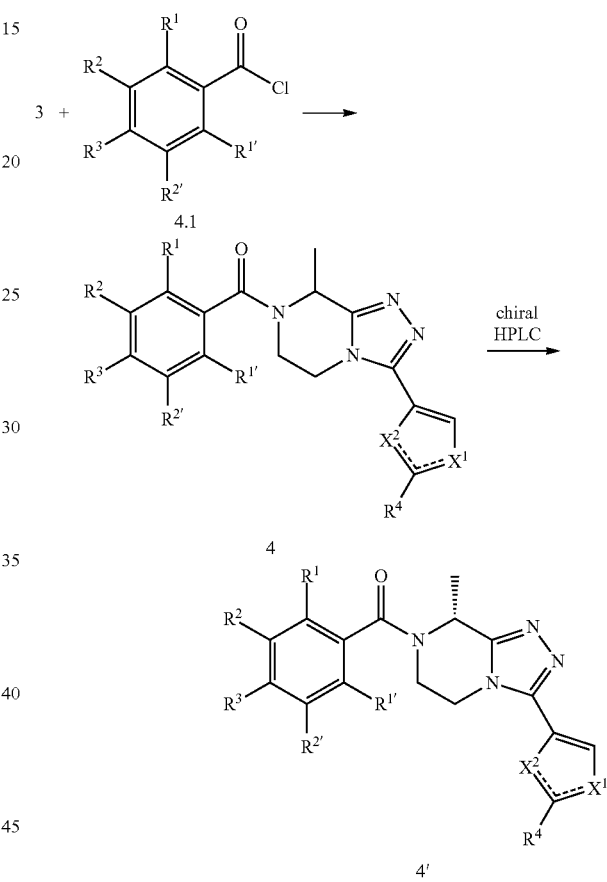

Step 1: In a round-bottom flask equipped with a condenser, imino-ether 1 (1 eq.) is dissolved in anhydrous MeOH, to which is added 2 (1 eq.) in one portion. The resulting solution is stirred at reflux overnight. Thereafter, the reaction mixture is brought to RT and the volatiles are removed under reduced pressure. The crude compound is then purified using silica gel chromatography to afford the desired product 3.1.

Step 2: In a round-bottom flask containing DCM is added 3.1 (1 eq.). Then, TFA (5 to 75 eq.), is added to the reaction mixture at RT. After 30 min stirring, the mixture is concentrated. Then DCM is added to the residue thus obtained, and washed with saturated NaHCO$_3$. The aqueous layer is extracted twice with DCM, the organic layers are washed with brine, dried over MgSO$_4$, filtered and concentrated under reduced pressure to obtain crude 3. The crude 3 may be directly used in the next step without further purification.

I.5. Step 4: Acylation Leading to Final Products

Method D: Acylation and Chiral HPLC Purification

Method D is the procedure used for the synthesis of the racemic product 4 and its purification to obtain (R)-enantiomer 4' compounds of general Formula I. Method D is detailed below:

Scheme 5: Acylation and chiral HPLC purification.

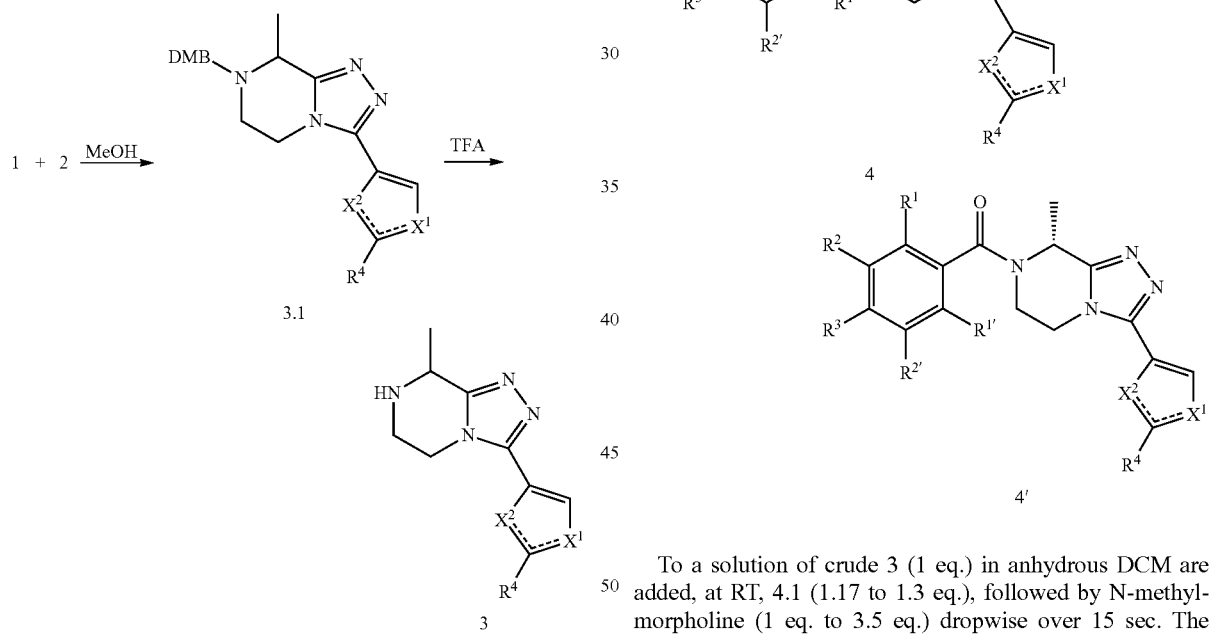

To a solution of crude 3 (1 eq.) in anhydrous DCM are added, at RT, 4.1 (1.17 to 1.3 eq.), followed by N-methylmorpholine (1 eq. to 3.5 eq.) dropwise over 15 sec. The reaction mixture is stirred at RT for 1 to 30 minutes and the milky suspension is poured into 1 M HCl solution or directly diluted with DCM. The aqueous phase is extracted with DCM. The organic phases are combined, optionally washed with 1 M NaOH, water, brine, dried over MgSO$_4$ and evaporated to dryness. The residue is solubilized in DCM and Et$_2$O and is slowly added to induce precipitation. The solid was filtered off, washed with Et$_2$O and dried under vacuum to afford 4. Alternatively, the residue is preliminary purified on silica gel before precipitation or purified on silica gel only.

Compound 4 may be purified by chiral preparative HPLC according to the abovementioned method to yield the corresponding chiral product (R)-4'. Compounds 4 and 4' are compounds of Formula I of the invention.

II. Chiral Synthesis
II.1. General Synthetic Scheme for Chiral Synthesis

Chiral compounds of the invention may be synthesized using the chiral process of the invention described in Scheme 6.

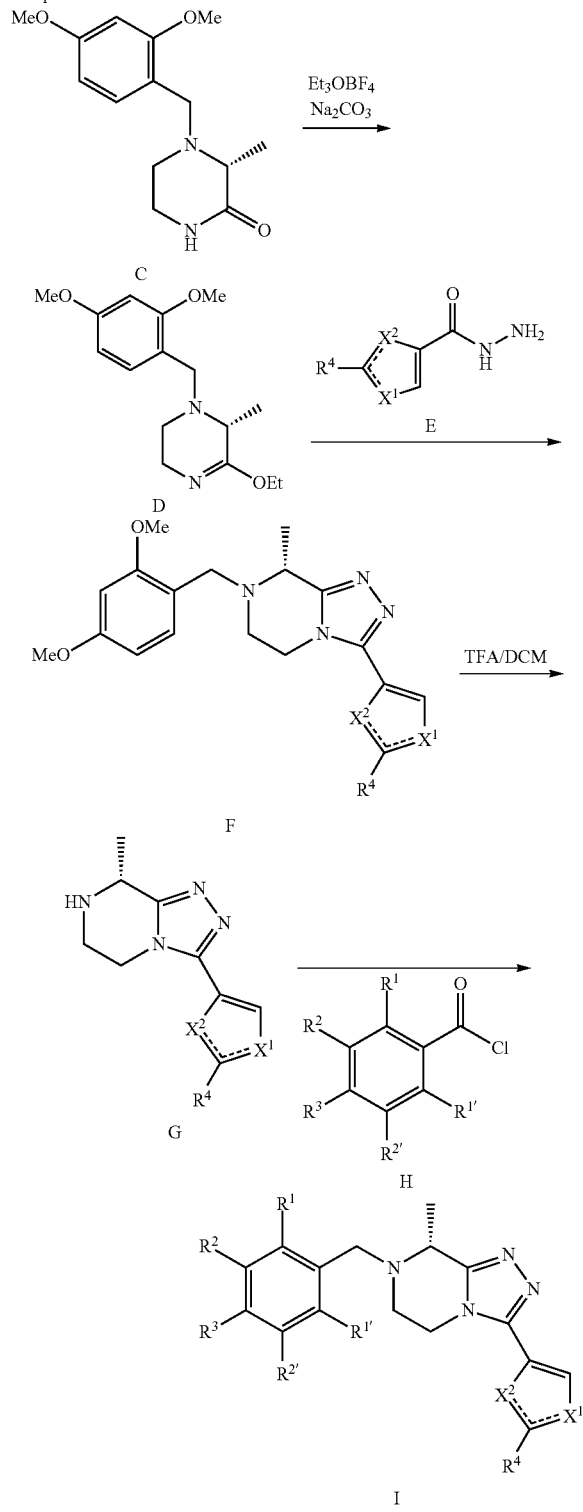

Scheme 6: General synthetic scheme for the preparation of chiral compounds of the invention.

DMB-protected chiral ketopiperazine C was converted to iminoether D by using the Meerwein reagent ($Et_3OBF_4$). Condensation reaction between the acyl hydrazide E and iminoether D was conducted under heating conditions in methanol to provide DMB protected piperazine F that was subsequently deprotected with TFA to yield compound of Formula G. Acylation with the appropriate acid chloride H afforded the final (R)-enantiomer typically in >90% enantiomeric excess (chiral HPLC).

II.2. Step 1: Conversion to Iminoether D
Method E: Conversion to Iminoether

General Method E is the procedure used for the synthesis of intermediate D.

Scheme 7: Conversion to iminoether D.

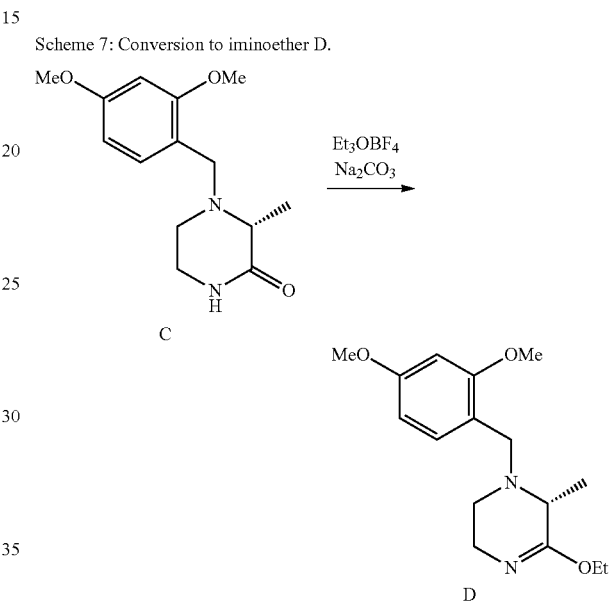

Synthesis of (R)-1-(2,4-dimethoxybenzyl)-5-ethoxy-6-methyl-1,2,3,6-tetrahydropyrazine D Oven dried (115° C.) sodium carbonate (2.48 g, 23.40 mmol, 2.25 eq.) was placed in a round-bottom flask. The round-bottom flask was backfilled with Ar and then capped with a rubber septum. A solution of (R)-4-(2,4-dimethoxybenzyl)-3-methylpiperazin-2-one C (2.75 g, 10.40 mmol, 1 eq.) in anhydrous DCM (35 mL) was added, followed by freshly prepared triethyloxoniumtetrafluoroborate (2.48 g, 13.05 mmol, 1.25 eq.) in one portion. Thereafter the reaction mixture was stirred further at RT for 45 min to 1 hour, whereupon the reaction mixture was diluted with saturated aqueous $NaHCO_3$ (100 mL). The aqueous layer was extracted with DCM (3×200 mL). The organic layers were combined, dried over $MgSO_4$, filtered and concentrated under reduced pressure to afford 3.1 g of yellow oil. The crude compound was then purified on silica gel (EtOAc/MeOH: 99/1) to afford the desired product D as a pale yellow oil. Yield: 1.44 g, 48%. LCMS: P=95%, retention time=1.8 min, $(M+H2O+H)^+$: 311; chiral HPLC retention time=12.3 min, ee>97%. $^1$H-NMR ($CDCl_3$): δ 7.23 (d, J=8.8, 1H), 6.48 (d, J=8.8, 1H), 6.44 (s, 1H), 4.02 (m, 2H), 3.92 (s, 6H), 3.86 (d, $J_{AB}$=14.0, 1H), 3.46 (d, $J_{AB}$=14.0, 1H), 3.44 (m, 2H), 3.10 (m, 1H), 2.79 (m, 1H), 2.32 (m, 1H), 1.35 (d, J=6.8, 3H), 1.24 (t, J=6.0, 3H).

The reaction mixture may alternatively be treated with brine. After stirring for about 20 min, additional water and DCM were added leading to phase separation. The organic layers were then dried over MgSO₄, filtered and concentrated under reduced pressure. The crude compound was then purified using flash chromatography on silica gel.

II.3. Step 2: Cyclodehydration Leading to F

Method F: Cyclodehydration

General Method F is the general procedure used for the synthesis of chiral triazolopiperazine intermediates F.

Scheme 8: Formation of acylhydrazide F.

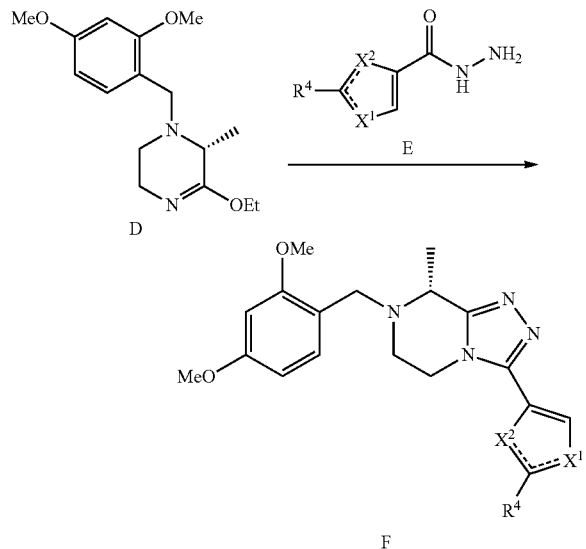

In a round-bottom flask equipped with a condenser, imino-ether D (1 eq.) was dissolved in anhydrous MeOH, to which was added E (1 eq.) in one portion. The resulting solution was stirred at a temperature ranging from 55° C. to 70° C. for a period of time ranging from 6 hours to 34 hours. Completion of the reaction was monitored by HPLC analysis. The reaction mixture was cooled down to RT and the solvent was removed under reduced pressure. The crude compound was then purified by silica gel chromatography to afford the desired product F.

In an embodiment of the invention, the crude compound precipitates during cooling of the reaction mixture. In this case, the precipitate is stirred at RT in MeOH for about 5 hours before being filtered, washed with MeOH and oven dried.

II.4. Step 3: Deprotection Leading to Triazolopiperazine G

Scheme 9: Deprotection.

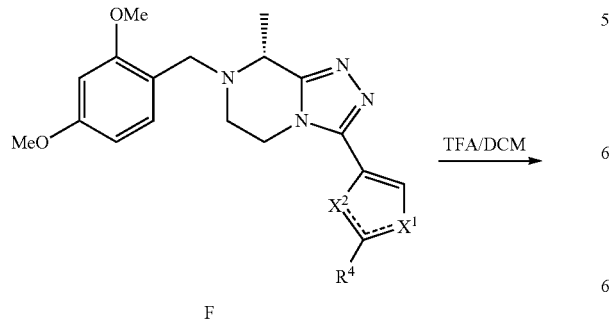

Method G: DMB Deprotection—TFA/DCM

Deprotection may be performed using TFA. In this case, F was dissolved in DCM. TFA (7.6 eq.) was added to the DCM solution of F at RT. The mixture was stirred at RT for 2 h-2 h30. Completion of the deprotection was monitored by HPLC. Water was added, the mixture stirred for 30 minutes and filtered. The filter cake was washed with water and DCM. The filtrate layers were separated. The pH of the aqueous layer was adjusted to 12-13 by the addition of 4M NaOH. Sodium chloride was then added and the aqueous solution was extracted with DCM. The DCM extract comprising G was concentrated and was used in the next step without further purification.

II.5. Step 4: Acylation Leading to Final Products

Method H: Acylation NMM/DCM

General Method H is the general procedure used for the synthesis of (R)-enantiomer of Formula I of the invention.

Scheme 10: Acylation.

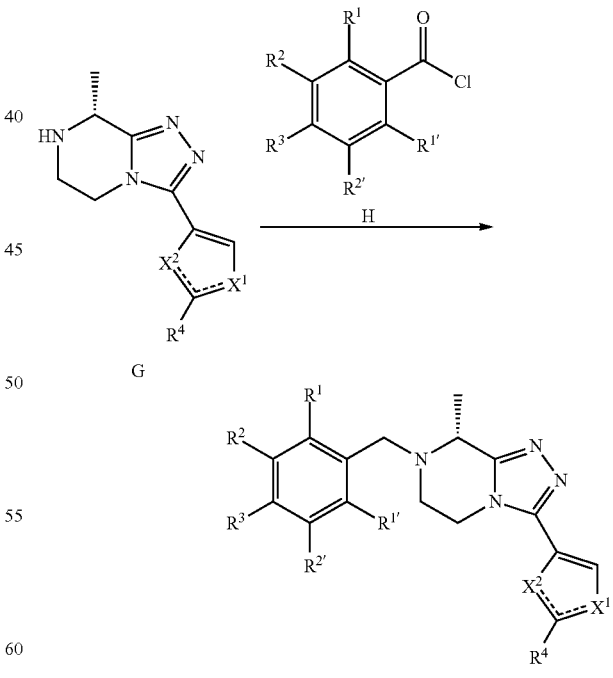

To a solution of crude G (1 eq.) in anhydrous DCM were added at 0° C. H (1.3 eq.), followed by N-methylmorpholine (2.2 eq.) dropwise over 15 sec. The reaction mixture was stirred at RT for 10 minutes and, the milky suspension was poured into 1 M HCl. The aqueous phase was extracted with DCM. The organic phases were combined, washed with 1 M NaOH, brine, dried over MgSO$_4$ and evaporated to dryness. The crude compound was purified by silica gel chromatography to afford the desired product (R)-I.

Measurement of % ee confirmed that no detectable racemization occurs during the acidolytic deprotection and N-acylation steps.

Method I: Acylation—Biphasic Conditions

Alternatively, the reaction may be performed under biphasic conditions.

In this case, saturated sodium hydrogen carbonate solution was added to the DCM slurry of G (1 eq.) at RT. H (1 eq.) was added and the mixture stirred for a period of time ranging from about 20 minutes to overnight at RT. Completion of the reaction was monitored by HPLC. The layers were separated and the DCM phase washed with water. The DCM extracts were dried with magnesium sulfate and filtered, washing the filter cake with DCM. The DCM extracts were then concentrated. TBME was added and the resulting slurry stirred overnight at RT. The solid was collected by filtration, washed with TBME and pulled dry. The crude compound may be purified by silica gel chromatography or by crystallisation.

Measurement of % ee confirmed that no detectable racemization occurs during the acidolytic deprotection and N-acylation steps.

III. Chemical Characterization

Compound 1: HPLC-MS: $t_R$=3.2 min, (M+H)$^+$=341; Chiral HPLC (Method B): % ee=99.2; $^1$H-NMR (CDCl$_3$): δ7.5 (m, 2H), 7.2 (m, 2H), 6.9 (m, 1H), 6.2 (m, 1H), 5.6 (m, 1H), 4.7 (m, 1H), 4.4 (m, 1H), 4.2 (m, 1H), 3.5 (m, 1H), 2.4 (s, 3H), 1.7 (d, 3H); $^{19}$F-NMR (CDCl$_3$): δ−96.4.

Compound 2: HPLC-MS: $t_R$=4.4 min, (M+H)$^+$=358; Chiral HPLC (Method A): % ee=97.1; $^1$H-NMR (CDCl$_3$): δ 8.0 (s, 1H), 7.5 (m, 2H), 7.1 (m, 2H), 5.7 (m, 1H), 4.9 (dd, 1H), 4.5 (m, 1H), 4.2 (td, 1H), 3.5 (td, 1H), 2.8 (s, 3H), 1.7 (d, 3H); $^{19}$F-NMR (CDCl$_3$): δ −98.0.

Compound 3: HPLC-MS: $t_R$=4.0 min, (M+H)$^+$=412; Chiral HPLC (Method B): % ee=97.2; $^1$H-NMR (CDCl$_3$): δ8.4 (s, 1H), 7.5 (m, 2H), 7.2 (m, 2H), 5.8 (m, 1H), 4.9 (dd, 1H), 4.6 (m, 1H), 4.3 (td, 1H), 3.5 (td, 1H), 1.7 (d, 3H); $^{19}$F-NMR (CDCl$_3$): δ−58.3, 98.2.

Compound 4: HPLC-MS: $t_R$=3.4 min, (M+H)$^+$=359; Chiral HPLC (Method B): % ee=97.2; $^1$H-NMR (CDCl$_3$): δ7.0 (m, 1H), 6.2 (m, 1H), 5.1 (m, 1H), 4.4 (m, 1H), 4.1 (m, 1H), 3.8-3.4 (m, 1H), 2.4 (s, 3H), 1.7 (m, 3H); $^{19}$F-NMR (CDCl$_3$): δ−54.2, −56.3, −67.1, −71.1.

Compound 5: HPLC-MS: $t_R$=3.9 min, (M+H)$^+$=359; Chiral HPLC (Method B): % ee=97.1; $^1$H-NMR (CDCl$_3$): δ7.4 (m, 3H), 7.0 (d, 1H), 6.2 (d, 1H), 5.6 (m, 1H), 4.6 (m, 1H), 4.4 (dd, 1H), 4.2 (td, 1H), 3.5 (td, 1H), 2.4 (s, 3H), 1.7 (d, 3H); $^{19}$F-NMR (CDCl$_3$): δ−71.7, −74.3.

Compound 6: HPLC-MS: $t_R$=4.1 min, (M+H)$^+$=377; Chiral HPLC (Method B): % ee=98.1; $^1$H-NMR (CDCl$_3$): δ7.1 (m, 2H), 7.0 (d, 1H), 6.2 (d, 1H), 6.1 (m, 1H), 5.1-5.0 (m, 1H), 4.5 (m, 1H), 4.2 (m, 1H), 3.8-3.7 (m, 1H), 2.4 (s, 3H), 1.7 (m, 3H).

Compound 7: HPLC-MS: $t_R$=4.2 min, (M+H)$^+$=377; Chiral HPLC (Method B): % ee=98.7; $^1$H-NMR (CDCl$_3$): δ7.1 (m, 2H), 7.0 (d, 1H), 6.2 (d, 1H), 5.6 (m, 1H), 4.6 (m, 1H), 4.5 (dd, 1H), 4.2 (td, 1H), 3.5 (td, 1H), 2.4 (s, 3H), 1.7 (d, 3H); $^{19}$F-NMR (CDCl$_3$): δ−75.7.

Compound 8: HPLC-MS: $t_R$=4.2 min, (M+H)$^+$=375; Chiral HPLC (Method B): % ee=98.1; $^1$H-NMR (CDCl$_3$): δ7.6 (m, 1H), 7.4 (m, 1H), 7.2 (m, 1H), 7.0 (d, 1H), 6.2 (d, 1H), 5.6 (m, 1H), 4.6 (m, 1H), 4.5 (dd, 1H), 4.2 (td, 1H), 3.5 (td, 1H), 2.4 (s, 3H), 1.7 (d, 3H); $^{19}$F-NMR (CDCl$_3$): δ−96.1.

Compound 9: HPLC-MS: $t_R$=4.2 min, (M+H)$^+$=375; Chiral HPLC (Method B): % ee=98.1; $^1$H-NMR (CDCl$_3$): δ7.5 (m, 1H), 7.3 (m, 1H), 7.2 (m, 1H), 7.0 (d, 1H), 6.2 (d, 1H), 5.6 (m, 1H), 4.6 (m, 1H), 4.4 (dd, 1H), 4.2 (td, 1H), 3.5 (td, 1H), 2.4 (s, 3H), 1.7 (d, 3H); $^{19}$F-NMR (CDCl$_3$): δ−94.2.

Compound 10: HPLC-MS: $t_R$=4.1 min, (M+H)$^+$=357; Chiral HPLC (Method B): % ee=98.3; $^1$H-NMR (CDCl$_3$): δ7.4 (m, 4H), 7.0 (d, 1H), 6.2 (d, 1H), 5.6 (m, 1H), 4.6 (m, 1H), 4.4 (dd, 1H), 4.2 (td, 1H), 3.4 (td, 1H), 2.4 (s, 3H), 1.7 (d, 3H).

Compound 11: HPLC-MS: $t_R$=4.4 min, (M+H)$^+$=391; Chiral HPLC (Method B): % ee=97.7; $^1$H-NMR (CDCl$_3$): δ7.6 (m, 2H), 7.2 (m, 1H), 7.0 (d, 1H), 6.2 (d, 1H), 5.6 (m, 1H), 4.6 (m, 1H), 4.5 (dd, 1H), 4.2 (td, 1H), 3.5 (td, 1H), 2.4 (s, 3H), 1.7 (d, 3H).

Compound 12: HPLC-MS: $t_R$=4.9 min, (M+H)$^+$=466; Chiral HPLC (Method B): % ee=96.7; $^1$H-NMR (CDCl$_3$): δ8.4 (s, 1H), 7.1 (m, 1H), 6.1 (m, 1H), 5.2-5.1 (m, 1H), 4.9 (dd, 1H), 4.2 (m, 1H), 3.9-3.5 (m, 1H), 1.8 (m, 3H); $^{19}$F-NMR (CDCl$_3$): δ−58.3, −71.1.

Compound 13: HPLC-MS: $t_R$=4.6 min, (M+H)$^+$=430; Chiral HPLC (Method B): % ee=96.3; $^1$H-NMR (CDCl$_3$): δ8.4 (s, 1H), 7.3 (m, 3H), 5.7 (m, 1H), 4.9 (dd, 1H), 4.5 (m, 1H), 4.3 (td, 1H), 3.6 (td, 1H), 1.8 (d, 3H); $^{19}$F-NMR (CDCl$_3$): δ−58.3, −71.8, −73.6.

Compound 14: HPLC-MS: $t_R$=4.8 min, (M+H)$^+$=448; Chiral HPLC (Method B): % ee=95.2; $^1$H-NMR (CDCl$_3$): δ8.5 (s, 1H), 7.1 (m, 3H), 6.2 (m, 1H), 5.2-5.1 (m, 1H), 4.9 (dd, 1H), 4.2 (m, 1H), 3.9-3.4 (m, 1H), 1.8 (m, 3H); $^{19}$F-NMR (CDCl$_3$): δ−58.3, −77.4.

Compound 15: HPLC-MS: $t_R$=4.86 min, (M+H)$^+$=448; Chiral HPLC (Method B): % ee=95.4; $^1$H-NMR (CDCl$_3$): δ8.5 (s, 1H), 7.2 (m, 3H), 6.2 (m, 1H), 5.2-5.1 (m, 1H), 4.9 (dd, 1H), 4.2 (m, 1H), 3.9-3.5 (m, 1H), 1.8 (m, 3H); $^{19}$F-NMR (CDCl$_3$): δ−58.3, −77.1.

Compound 16: HPLC-MS: $t_R$=4.8 min, (M+H)$^+$=446; Chiral HPLC (Method B): % ee=95.8; $^1$H-NMR (CDCl$_3$): δ8.4 (s, 1H), 7.6 (m, 1H), 7.4 (m, 1H), 7.3 (m, 1H), 5.7 (m, 1H), 4.9 (dd, 1H), 4.6 (m, 1H), 4.3 (td, 1H), 3.6 (td, 1H), 1.8 (d, 3H); $^{19}$F-NMR (CDCl$_3$): δ−58.3, −96.0.

Compound 17: HPLC-MS: $t_R$=4.9 min, (M+H)$^+$=446; Chiral HPLC (Method B): % ee=95.4; $^1$H-NMR (CDCl$_3$): δ8.5 (s, 1H), 7.5 (m, 1H), 7.3 (m, 1H), 7.2 (m, 1H), 5.7 (m, 1H), 4.9 (dd, 1H), 4.5 (m, 1H), 4.3 (td, 1H), 3.6 (td, 1H), 1.8 (d, 3H); $^{19}$F-NMR (CDCl$_3$): δ−58.3, −94.2.

Compound 18: HPLC-MS: $t_R$=4.8 min, (M+H)$^+$=428; Chiral HPLC (Method B): % ee=96.4; $^1$H-NMR (CDCl$_3$): δ8.4 (s, 1H), 7.4 (m, 4H), 5.7 (m, 1H), 4.8 (dd, 1H), 4.5 (m, 1H), 4.2 (td, 1H), 3.5 (td, 1H), 1.7 (d, 3H); $^{19}$F-NMR (CDCl$_3$): δ−58.3.

\* \* \*

BIOLOGY EXAMPLES

Functional Assay

Aequorin Assay with Human NK-3 Receptor

Changes in intracellular calcium levels are a recognized indicator of G protein-coupled receptor activity. The efficacy of compounds of the invention to inhibit NKA-mediated NK-3 receptor activation was assessed by an in vitro Aequorin functional assay. Chinese Hamster Ovary recombinant cells expressing the human NK-3 receptor and a construct that encodes the photoproteinapoaequorin were used for this assay. In the presence of the cofactor coelenterazine, apoaequorin emits a measurable luminescence that is proportional to the amount of intracellular (cytoplasmic) free calcium.

Antagonist Testing

The antagonist activity of compounds of the invention is measured following pre-incubation (3 minutes) of the compound (at various concentrations) with the cells, followed by addition of the reference agonist (NKA) at a final concentration equivalent to the $EC_{80}$ (3 nM) and recording of emitted light (FDSS 6000 Hamamatsu) over the subsequent 90-second period. The intensity of the emitted light is integrated using the reader software. Compound antagonist activity is measured based on the concentration-dependent inhibition of the luminescence response to the addition of Neurokinin A.

Inhibition curves are obtained for compounds of the invention and the concentrations of compounds which inhibit 50% of reference agonist response ($IC_{50}$) were determined (see results in Table 2 below). The $IC_{50}$ values shown in Table 2 indicate that compounds of the invention are potent NK-3 antagonist compounds.

Competitive Binding Assays

The affinity of compounds of the invention for the human NK-3 receptor was determined by measuring the ability of compounds of the invention to competitively and reversibly displace a well-characterized NK-3 radioligand in a concentration-dependent manner.

$^3$H-SB222200 Binding Competition Assay with Human NK-3 Receptor

The ability of compounds of the invention to inhibit the binding of the NK-3 receptor selective antagonist $^3$H-SB222200 was assessed by an in vitro radioligand binding assay. Membranes were prepared from Chinese hamster ovary recombinant cells stably expressing the human NK-3 receptor. The membranes were incubated with 5 nM $^3$H-SB222200 (ARC) in a HEPES 25 mM/NaCl 0.1M/$CaCl_2$ 1 mM/$MgCl_2$ 5 mM/BSA 0.5%/Saponin 10 μg/ml buffer at pH 7.4 and various concentrations of compounds of the invention. The amount of $^3$H-SB222200 bound to the receptor was determined after filtration by the quantification of membrane associated radioactivity using the TopCount-NXT reader (Packard). Competition curves were obtained for compounds of the invention and the concentration that displaced 50% of bound radioligand ($IC_{50}$) were determined by linear regression analysis and then the apparent inhibition constant (Ki) values were calculated by the following equation: $K_i = IC_{50}/(1+[L]/K_d)$ where [L] is the concentration of free radioligand and $K_d$ is its dissociation constant at the receptor, derived from saturation binding experiments (Cheng and Prusoff, 1973) (see results in Table 2 below).

Table 2 shows biological results obtained using the $^3$H-SB222200 binding competition assay with compounds of the invention. These results indicate that compounds of the invention display potent affinity for the human NK-3 receptor.

TABLE 2

| Cpd n° | Functional assay: Aequorin assay with human NK-3 receptor hNK-3 - AEQ (antagonist $IC_{50}$, nM) | Competitive binding assay with human NK-3 receptor hNK-3 ($K_i$, nM) |
|---|---|---|
| 1 | 60 | 48 |
| 2 | 160 | 100 |
| 3 | 20 | 22 |
| 4 | 72 | 52 |
| 5 | 52 | 42 |
| 6 | 99 | 74 |
| 7 | 57 | 33 |
| 8 | 62 | 44 |
| 9 | 53 | 38 |
| 10 | 74 | 36 |
| 11 | 36 | 27 |
| 12 | 33 | 29 |
| 13 | 26 | 20 |
| 14 | 59 | 40 |
| 15 | 24 | 13 |
| 16 | 23 | 14 |
| 17 | 37 | 22 |
| 18 | 31 | 21 |

Selectivity Assay

Selectivity of the compounds of the invention was determined over the other human NK receptors, namely NK-1 and NK-2 receptors.

Human NK-1

The affinity of compounds of the invention for the NK-1 receptor was evaluated in CHO recombinant cells which express the human NK-1 receptor. Membrane suspensions were prepared from these cells. The following radioligand: [$^3$H] substance P (PerkinElmer Cat#NET111520) was used in this assay. Binding assays were performed in a 50 mM Tris/5 mM $MnCl_2$/150 mM NaCl/0.1% BSA at pH 7.4. Binding assays consisted of 25 μl of membrane suspension (approximately 5 μg of protein/well in a 96 well plate), 50 μl of compound or reference ligand (Substance P) at increasing concentrations (diluted in assay buffer) and 2 nM [$^3$H] substance P. The plate was incubated 60 min at 25° C. in a water bath and then filtered over GF/C filters (Perkin Elmer, 6005174, presoaked in 0.5% PEI for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand ($IC_{50}$) were determined and then apparent inhibition constant Ki values were calculated by the following equation: $K_i = IC_{50}/(1+[L]/K_D)$ where [L] is the concentration of free radioligand and $K_D$ is its dissociation constant at the receptor, derived from saturation binding experiments (Cheng and Prusoff, 1973).

Human NK-2

The affinity of compounds of the invention for the NK-2 receptor was evaluated in CHO recombinant cells which express the human NK-2 receptor. Membrane suspensions were prepared from these cells. The following radioligand [$^{125}$I]-Neurokinin A (PerkinElmer Cat#NEX252) was used in this assay. Binding assays were performed in a 25 mM HEPES/1 mM $CaCl_2$/5 mM $MgCl_2$/0.5% BSA/10 μg/ml saponin, at pH 7.4. Binding assays consisted of 25 μl of membrane suspension (approximately 3.75 μg of protein/well in a 96 well plate), 50 μl of compound or reference ligand (Neurokinin A) at increasing concentrations (diluted in assay buffer) and 0.1 nM [$^{125}$I]-Neurokinin A. The plate was incubated 60 min at 25° C. in a water bath and then filtered over GF/C filters (Perkin Elmer, 6005174, presoaked in assay buffer without saponine for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand ($IC_{50}$) were determined and then apparent inhibition constant Ki values were calculated by the following equation: $Ki=IC_{50}/(1+[L]/K_D)$ where [L] is the concentration of free radioligand and $K_D$ is its dissociation constant at the receptor, derived from saturation binding experiments (Cheng and Prusoff, 1973).

The compounds of the invention, which were tested in the above NK-1 and NK-2 described assays, demonstrated a low affinity at the human NK-1 and human NK-2 receptors: more than 100 fold shift of the Ki compared to the human NK-3 receptor (table 3). Thus, compounds according to the invention have been shown to be selective over NK-1 and NK-2 receptors.

TABLE 3

| Cpd n° | hNK-3 ($K_i$, nM) | hNK-1 ($K_i$, nM) | hNK-2 ($K_i$, nM) |
| --- | --- | --- | --- |
| 1 | 48 | >30000 | 52000 |
| 2 | 100 | >30000 | >30000 |
| 3 | 22 | >30000 | 6600 |
| 4 | 52 | >30000 | 30000 |
| 5 | 42 | >30000 | 31000 |
| 6 | 74 | >30000 | >30000 |
| 7 | 33 | 27000 | 21000 |
| 8 | 44 | 18000 | 9100 |
| 9 | 38 | 13000 | 14000 |
| 10 | 36 | 25000 | 23000 |
| 11 | 27 | 6900 | 4200 |
| 12 | 29 | 19000 | 4700 |
| 13 | 20 | 21000 | 7000 |
| 14 | 40 | 28000 | 15000 |
| 15 | 13 | 24000 | 3500 |
| 16 | 14 | 9400 | 1500 |
| 17 | 22 | 12000 | 5200 |
| 18 | 21 | 15000 | 5900 | hERG Inhibition Assay

The human ether-a-go-go related gene (hERG) encodes the inward rectifying voltage gated potassium channel in the heart ($I_{Kr}$) which is involved in cardiac repolarisation. $I_{Kr}$ current inhibition has been shown to elongate the cardiac action potential, a phenomenon associated with increased risk of arrhythmia. $I_{Kr}$ current inhibition accounts for the vast majority of known cases of drug-induced QT-prolongation. A number of drugs have been withdrawn from late stage clinical trials due to these cardiotoxic effects, therefore it is important to identify inhibitors early in drug discovery.

The hERG inhibition study aims at quantifying the in vitro effects of compounds of the invention on the potassium-selective $IK_r$ current generated in normoxic conditions in stably transfected HEK 293 cells with the human ether-a-go-go-related gene (hERG).

Whole-cell currents (acquisition by manual patch-clamp) elicited during a voltage pulse were recorded in baseline conditions and following application of tested compounds (5 minutes of exposure). The concentrations of tested compounds (0.3 μM; 3 μM; 10 μM; 30 μM) reflect a range believed to exceed the concentrations at expected efficacy doses in preclinical models.

The pulses protocol applied is described as follow: the holding potential (every 3 seconds) was stepped from −80 mV to a maximum value of +40 mV, starting with −40 mV, in eight increments of +10 mV, for a period of 1 second. The membrane potential was then returned to −55 mV, after each of these incremented steps, for 1 second and finally repolarized to −80 mV for 1 second.

The current density recorded were normalized against the baseline conditions and corrected for solvent effect and time-dependent current run-down using experimental design in test compound free conditions.

Inhibition curves were obtained for compounds and the concentrations which decreased 50% of the current density determined in the baseline conditions ($IC_{50}$) were determined. All compounds for which the $IC_{50}$ value is above 10 μM are not considered to be potent inhibitors of the hERG channel whereas compounds with $IC_{50}$ values below 1 μM are considered potent hERG channel inhibitors.

When tested in the hERG inhibition assay, compounds of the invention were determined to have $IC_{50}$ values as shown in Table 4.

Determination of Plasma Protein Binding

The pharmacokinetic and pharmacodynamic properties of chemicals/drugs are largely a function of the reversible binding of chemicals to plasma or serum proteins. Generally, only the unbound or "free fraction" of a drug is available for diffusion or transport across cell membranes, and for interaction with a pharmacological/toxicological target. Consequently, the extent of the plasma protein binding (PPB) of a compound influences its action as well as its distribution and elimination.

The determination of plasma protein binding (PPB) of a compound is enabled by equilibrium dialysis, an accepted and standard method for reliable estimation of the non-bound drug fraction in plasma. RED (Rapid Equilibrium Dialysis) device insert is made of two side-by-side chambers separated by an O-ring-sealed vertical cylinder of dialysis membrane (MWCO~8,000). Plasma containing drug (at 5 μM or blood concentrations otherwise corresponding to efficacious doses, if known) is added to one chamber while buffer is added to the second. After 4 hours incubation at 37° C. under shaking, an aliquot is removed from each chamber and analyzed by a LC-MS/MS procedure enables the determination of both free and bound drug.

The percentages provided in Table 4 represent for the compounds of the invention the bound drug fraction to the plasma protein. The "free fraction" may be calculated as 100%−% rPPB (i.e. the complementary percentage of that disclosed in Table 4, corresponding to the drug concentration that is unbound and therefore available to engage biological target and elicit pharmacological activity).

TABLE 4

| Cpd n° | Exposure (% rPPB) | CardioSafety (hERG $IC_{50}$, μM) |
| --- | --- | --- |
| 1 | 28 | 31 |
| 2 | 17 | NA |
| 3 | 50 | 70 |
| 4 | 30 | NA |
| 5 | 27 | NA |
| 6 | 37 | NA |
| 7 | 26 | NA |
| 8 | 47 | NA |
| 9 | 68 | NA |
| 10 | 56 | NA |
| 11 | 76 | NA |
| 12 | 67 | NA |
| 13 | 51 | NA |
| 14 | 69 | NA |
| 15 | 60 | NA |
| 16 | 82 | NA |

TABLE 4-continued

| Cpd n° | Exposure (% rPPB) | CardioSafety (hERG IC$_{50}$, μM) |
|---|---|---|
| 17 | 84 | NA |
| 18 | 78 | NA |

NA: not available

In vivo Assay to Assess Compound Activity in Rat (Oral Dosing)

The effect of compounds of the invention to inhibit luteinizing hormone (LH) secretion is determined by the following biological studies.

Castrated Male Rat Model to Assess the Effect of Compound of Invention on Circulating Levels of Luteinizing Hormone (LH)

In humans and rodents, castration is well-precedented to permit heightened, persistent GnRH signaling and consequent elevation of circulating LH. Thus, a castrated rat model is used to provide a broad index for measurement of LH inhibition as a marker of test compound inhibition of the GnRH signaling pathway.

Castrated adult male Sprague-Dawley (SD) rats (150-175 g) were purchased from Janvier (St Berthevin, France). All animals were housed 2 per cage in a temperature-controlled room (22±2° C.) and 50±5% relative humidity with a 12 hour/12 hour light/dark cycles (lights off at 6 h00 pm). The animals were allowed 3 weeks of postoperative recovery prior to study. Animals were handled on a daily basis. Standard diet and tap water were provided ad libitum. Animal cage litters were changed once a week. On the study day, animals were acclimated to the procedure room for a period of one hour prior to the initiation of the experiment.

Compounds of the invention were formulated in 0.5% methyl cellulose.

After basal sampling (TO) a single dose of compounds of the invention or vehicle was administrated orally to rats. Blood samples were then collected at several time points post dosing (45, 90, 150, 300 and 420 minutes). Blood samples were obtained via tail vein bleed, drawn into EDTA-containing tubes and centrifuged immediately. Plasma samples were collected and stored in a −80° C. freezer until assayed. Serum LH levels were determined using radioimmunoassay kit from RIAZEN—Rat LH, Zentech (Liège, Belgium). Baseline was defined as the initial basal blood sample.

When tested in the castrated male rat model described above, compound no. 1 of the invention significantly suppressed circulating LH levels (statistically significant, p<0.05) at a dose less than or equal to 30 mg/kg).

The invention claimed is:

1. A compound of Formula I:

[Structure of Formula I]

or a pharmaceutically acceptable solvate thereof, wherein:
R$^1$ is H or F;
R$^{1'}$ is H;
R$^2$ is H, F or Cl;
R$^{2'}$ is H or F;
R$^3$ is F or Cl;
R$^4$ is methyl or trifluoromethyl;
X$^1$ is S and X$^2$ is N, or X$^1$ is CH and X$^2$ is O;
═══ represents a single or a double bond depending on X$^1$ and X$^2$; and
*--- represents an (R)-enantiomer or a racemate of the compound of Formula I.

2. The compound according to claim 1, having Formula I' or Formula I":

[Structure of Formula I']

[Structure of Formula I"]

or a pharmaceutically acceptable solvate thereof, wherein
R$^1$ is H or F;
R$^{1'}$ is H;
R$^2$ is H, F or Cl;
R$^{2'}$ is H or F;
R$^3$ is F or Cl;
R$^4$ is methyl or trifluoromethyl;
X$^1$ is S and X$^2$ is N, or X$^1$ is CH and X$^2$ is O; and
═══ represents a single or a double bond depending on X$^1$ and X$^2$.

3. The compound according to claim 1, having Formula Ia:

[Structure of Formula Ia]

or a pharmaceutically acceptable solvate thereof, wherein:
R$^1$ is H or F;
R$^{1'}$ is H;
R$^2$ is H, F or Cl;
R$^{2'}$ is H or F;
R$^3$ is F or Cl;
R$^4$ is methyl or trifluoromethyl; and

*--- represents an (R)-enantiomer or a racemate of the compound of Formula Ia.

4. The compound according to claim 1, selected from Formula Ia':

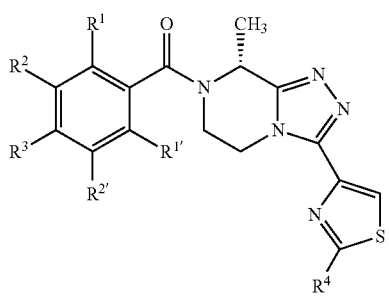

or a pharmaceutically acceptable solvate thereof, wherein
R$^1$ is H or F;
R$^{1'}$ is H;
R$^2$ is H, F or Cl;
R$^{2'}$ is H or F;
R$^3$ is F or Cl; and
R$^4$ is methyl or trifluoromethyl.

5. The compound according to claim 1, having Formula Ib:

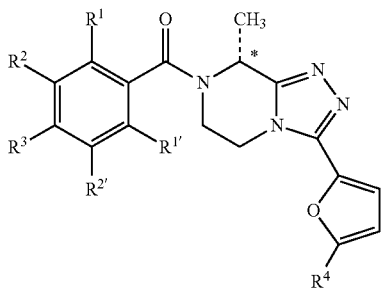

or a pharmaceutically acceptable solvate thereof, wherein:
R$^1$ is H or F;
R$^{1'}$ is H;
R$^2$ is H, F or Cl;
R$^{2'}$ is H or F;
R$^3$ is F or Cl;
R$^4$ is methyl or trifluoromethyl; and

*--- represents an (R)-enantiomer or a racemate of the compound of Formula Ib.

6. The compound according to claim 1, having Formula Ib':

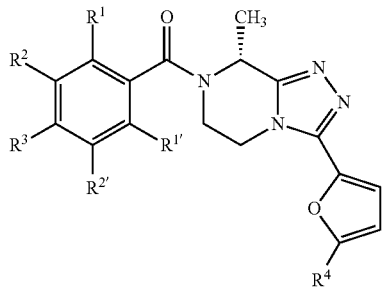

or a pharmaceutically acceptable solvate thereof, wherein
R$^1$ is H or F;
R$^{1'}$ is H;
R$^2$ is H, F or Cl;
R$^{2'}$ is H or F;
R$^3$ is F or Cl; and
R$^4$ is methyl or trifluoromethyl.

7. The compound according to claim 1, selected from the group consisting of:
(R)-(4-fluorophenyl) (8-methyl-3-(5-methylfuran-2-yl)-5,6-dihydro-[1,2,4]triazolo]4,3-a]pyrazin-7(8H)-yl) methanone;
(R)-(4-fluorophenyl) (8-methyl-3-(2-methylthiazol-4-yl)-5,6-dihydro-[1,2,4]triazolo[4,3-a]pyrazin-7(8H)-yl) methanone;
(R)-(4-fluorophenyl) (8-methyl-3-(2-(trifluoromethyl)thiazol-4-yl)-5,6-dihydro-[1,2,4]triazolo[4,3-a]pyrazin-7(8H)-yl)methanone;
(R)-(8-methyl-3-(5-methylfuran-2-yl)-5,6-dihydro-[1,2,4]triazolo[4,3-a]pyrazin-7(8H)-yl) (2,3,4,5-tetrafluorophenyl)methanone;
(R)-(3,4-difluorophenyl) (8-methyl-3-(5-methylfuran-2-yl)-5,6-dihydro-[1,2,4]triazolo[4,3-a]pyrazin-7(8H)-yl)methanone;
(R)-(8-methyl-3-(5-methylfuran-2-yl)-5,6-dihydro-[1,2,4]triazolo[4,3-a]pyrazin-7(8H)-yl) (2,3,4-trifluorophenyl)methanone;
(R)-(8-methyl-3-(5-methylfuran-2-yl)-5,6-dihydro-[1,2,4]triazolo[4,3-a]pyrazin-7(8H)-yl) (3,4,5-trifluorophenyl)methanone;
(R)-(3-chloro-4-fluorophenyl) (8-methyl-3-(5-methylfuran-2-yl)-5,6-dihydro-[1,2,4]triazolo[4,3-a]pyrazin-7(8H)-yl)methanone;
(R)-(4-chloro-3-fluorophenyl) (8-methyl-3-(5-methylfuran-2-yl)-5,6-dihydro-[1,2,4]triazolo[4,3-a]pyrazin-7(8H)-yl)methanone;
(R)-(4-chlorophenyl) (8-methyl-3-(5-methylfuran-2-yl)-5,6-dihydro-[1,2,4]triazolo[4,3-a]pyrazin-7(8H)-yl) methanone;
(R)-(3,4-dichlorophenyl) (8-methyl-3-(5-methylfuran-2-yl)-5,6-dihydro-[1,2,4]triazolo[4,3-a]pyrazin-7(8H)-yl)methanone;
(R)-(8-methyl-3-(2-(trifluoromethyl)thiazol-4-yl)-5,6-dihydro-[1,2,4]triazolo[4,3-a]pyrazin-7(8H)-yl) (2,3,4,5-tetrafluorophenyl)methanone;
(R)-(3,4-difluorophenyl) (8-methyl-3-(2-(trifluoromethyl)thiazol-4-yl)-5,6-dihydro-[1,2,4]triazolo[4,3-a]pyrazin-7(8H)-yl)methanone;
(R)-(8-methyl-3-(2-(trifluoromethyl)thiazol-4-yl)-5,6-dihydro-[1,2,4]triazolo[4,3-a]pyrazin-7(8H)-yl) (2,3,4-trifluorophenyl)methanone;

(R)-(8-methyl-3-(2-(trifluoromethyl)thiazol-4-yl)-5,6-dihydro-[1,2,4]triazolo[4,3-a]pyrazin-7(8H)-yl) (3,4,5-trifluorophenyl)methanone;

(R)-(3-chloro-4-fluorophenyl) (8-methyl-3-(2-(trifluoromethyl) thiazol-4-yl)-5,6-dihydro-[1,2,4]triazolo[4,3-a]pyrazin-7(8H)-yl)methanone;

(R)-(4-chloro-3-fluorophenyl) (8-methyl-3-(2-(trifluoromethyl) thiazol-4-yl)-5,6-dihydro-[1,2,4]triazolo[4,3-a]pyrazin-7(8H)-yl)methanone;

(R)-(4-chlorophenyl) (8-methyl-3-(2-(trifluoromethyl) thiazol-4-yl)-5,6-dihydro-[1,2,4]triazolo[4,3-a] pyrazin-7(8H)-yl)methanone;

and pharmaceutically acceptable solvates thereof.

8. A pharmaceutical composition or a medicament comprising a compound of Formula I

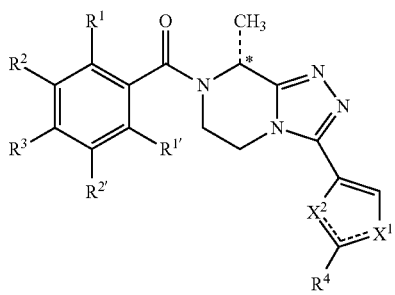

or a pharmaceutically acceptable solvate thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl;
$X^1$ is S and $X^2$ is N, or $X^1$ is CH and $X^2$ is O;
≡≡≡ represents a single or a double bond depending on $X^1$ and $X^2$; and
*--- represents an (R)-enantiomer or a racemate of the compound of Formula I, and
at least one pharmaceutically acceptable carrier, diluent, excipient and/or adjuvant.

9. A method for treating depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases selected from irritable bowel syndrome (IBS) and inflammatory bowel disorders, emesis, pre-eclampsia, airway related diseases selected from the group consisting of chronic obstructive pulmonary disease, asthma, airway hyperresponsiveness, bronchoconstriction and cough, urinary incontinence, contraception and sex hormone-dependent diseases selected from the group consisting of benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome, ovarian hyperthecosis, other manifestations of high intraovarian androgen concentrations selected from follicular maturation arrest, atresia, anovulation, dysmenorrhea, dysfunctional uterine bleeding and infertility, androgen-producing tumor, menorrhagia and adenomyosis,
comprising the administration, to a patient in need thereof, of a pharmaceutically effective amount of a compound of Formula I

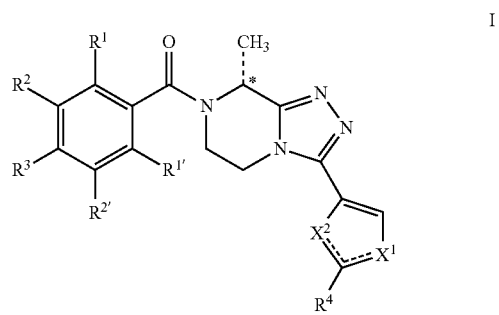

or a pharmaceutically acceptable solvate thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl;
$X^1$ is S and $X^2$ is N or $X^1$ is CH and $X^2$ is O;
≡≡≡ represents a single or a double bond depending on $X^1$ and $X^2$; and
*--- represents an (R)-enantiomer or a racemate of the compound of Formula I.

10. A method for treating hot flashes, comprising the administration, to a patient in need thereof, of a pharmaceutically effective amount of a compound of Formula I

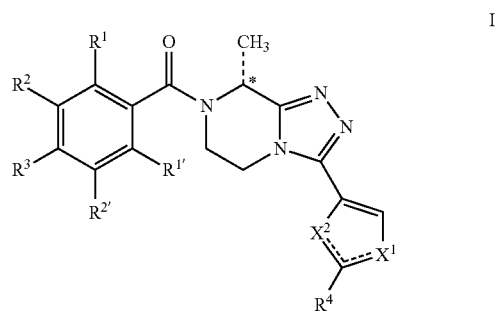

or a pharmaceutically acceptable solvate thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl;
$X^1$ is S and $X^2$ is N, or $X^1$ is CH and $X^2$ is O;
≡≡≡ represents a single or a double bond depending on $X^1$ and $X^2$; and
*--- represents an (R)-enantiomer or a racemate of the compound of Formula I.

11. The method according to claim 9, wherein the androgen-producing tumor is virilizing ovarian tumor or virilizing adrenal tumor.

12. A method for lowering the circulating luteinizing hormone (LH) levels, comprising administering to a patient in need thereof a pharmaceutically effective amount of a compound of Formula I,

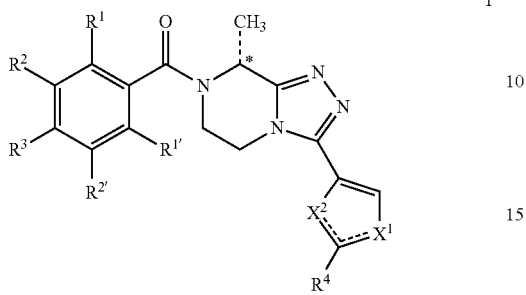

or a pharmaceutically acceptable solvate thereof, wherein:
$R^1$ is H or F;
$R^{1'}$ is H;
$R^2$ is H, F or Cl;
$R^{2'}$ is H or F;
$R^3$ is F or Cl;
$R^4$ is methyl or trifluoromethyl;
$X^1$ is S and $X^2$ is N, or $X^1$ is CH and $X^2$ is O;
═══ represents a single or a double bond depending on X1 and X2; and
*--- represents an (R)-enantiomer or a racemate of the compound of Formula I.

* * * * *

UNITED STATES PATENT AND TRADEMARK OFFICE
CERTIFICATE OF CORRECTION

PATENT NO. : 9,840,508 B2
APPLICATION NO. : 14/777543
DATED : December 12, 2017
INVENTOR(S) : Hamid Hoveyda, Guillaume Dutheuil and Graeme Fraser It is certified that error appears in the above-identified patent and that said Letters Patent is hereby corrected as shown below:

On the Title Page

"(73) Assignee: OGED SA, Charleroi (BE)"
Should be replaced with:
--(73) Assignee: OGEDA SA, Charleroi (BE)--

Signed and Sealed this
Seventeenth Day of April, 2018

Andrei Iancu
*Director of the United States Patent and Trademark Office*